United States Patent
Smith et al.

(10) Patent No.: US 12,281,983 B2
(45) Date of Patent: Apr. 22, 2025

(54) UAV-BORNE, HIGH-BANDWIDTH, LIGHTWEIGHT POINT SENSOR FOR QUANTIFYING GREENHOUSE GASES IN ATMOSPHERIC STRATA

(71) Applicant: SeekOps Inc., Austin, TX (US)

(72) Inventors: Brendan James Smith, Lakeway, TX (US); Victor Alexander Miller, II, Sonoma, CA (US); Andrew David Aubrey, Austin, TX (US)

(73) Assignee: SeekOps Inc., Austin, TX (US)

( * ) Notice: Subject to any disclaimer, the term of this patent is extended or adjusted under 35 U.S.C. 154(b) by 551 days.

(21) Appl. No.: 17/286,107

(22) PCT Filed: Oct. 22, 2019

(86) PCT No.: PCT/US2019/057305
§ 371 (c)(1),
(2) Date: Apr. 16, 2021

(87) PCT Pub. No.: WO2020/086499
PCT Pub. Date: Apr. 30, 2020

(65) Prior Publication Data
US 2021/0382475 A1   Dec. 9, 2021

Related U.S. Application Data

(60) Provisional application No. 62/748,647, filed on Oct. 22, 2018.

(51) Int. Cl.
*G01N 21/39* (2006.01)
*B64U 101/00* (2023.01)
(Continued)

(52) U.S. Cl.
CPC ............ *G01N 21/39* (2013.01); *G01N 21/85* (2013.01); *G01N 33/0016* (2013.01);
(Continued)

(58) Field of Classification Search
CPC .... G01N 21/39; G01N 21/85; G01N 33/0016; G01N 33/0062; G01N 2021/8578
See application file for complete search history.

(56) References Cited

U.S. PATENT DOCUMENTS 3,780,566 A   12/1973   Smith et al.
4,135,092 A   1/1979    Milly
(Continued)

FOREIGN PATENT DOCUMENTS

AU   3401499 A      11/1999
CN   101470072 A   7/2009
(Continued)

OTHER PUBLICATIONS

International Search Report and Written Opinion for PCT/US23/13893, mailed Jun. 30, 2023.
(Continued)

*Primary Examiner* — Kristina M Deherrera
*Assistant Examiner* — Jean F Morello
(74) *Attorney, Agent, or Firm* — Command IP LLP; Michael Zarrabian

(57) ABSTRACT

Systems, devices, and methods for a gas sensor comprising one or more optical cells; a processor having addressable memory, the processor configured to: detect gas from the one or more optical cells of the gas sensor, where the detected gas is one or more of: methane, carbon dioxide, hydrogen sulfide, water, ammonia, sulfur oxides, and nitrogen; record data corresponding to the detected gas, where the recorded data comprises at least one of: an ambient temperature from a temperature sensor, an ambient pressure from a pressure sensor, an aerial vehicle telemetry, and an aerial vehicle location from a global positioning system
(Continued)

(GPS); and generate a map of atmospheric greenhouse gas concentration on a map based on the detected gas and the recorded data.

20 Claims, 10 Drawing Sheets

(51) Int. Cl.
  *G01N 21/85* (2006.01)
  *G01N 33/00* (2006.01)
  *B64U 10/14* (2023.01)

(52) U.S. Cl.
  CPC ......... *G01N 33/0062* (2013.01); *B64U 10/14* (2023.01); *B64U 2101/00* (2023.01); *G01N 2021/8578* (2013.01)

(56) References Cited

U.S. PATENT DOCUMENTS

| | | | |
|---|---|---|---|
| 4,233,564 A | 11/1980 | Kerbel | |
| 4,507,558 A | 3/1985 | Bonne | |
| 4,988,833 A | 1/1991 | Lai | |
| 5,047,639 A | 9/1991 | Wong | |
| 5,075,619 A | 12/1991 | Said | |
| 5,173,749 A | 12/1992 | Tell et al. | |
| 5,291,265 A | 3/1994 | Kebabian | |
| 5,317,156 A | 5/1994 | Cooper et al. | |
| 5,767,780 A | 6/1998 | Smith et al. | |
| 5,822,058 A | 10/1998 | Adler-Golden et al. | |
| 6,064,488 A | 5/2000 | Brand et al. | |
| 6,295,859 B1 | 10/2001 | Hayden et al. | |
| 6,356,350 B1 | 3/2002 | Silver et al. | |
| 6,509,566 B1 | 1/2003 | Wamsley et al. | |
| 6,549,630 B1 | 4/2003 | Bobisuthi | |
| 7,162,933 B2 * | 1/2007 | Thompson ............ | G01N 1/2214 |
| | | | 73/863.11 |
| 7,800,751 B1 | 9/2010 | Silver et al. | |
| 7,833,480 B2 | 11/2010 | Blazewicz et al. | |
| 8,060,270 B2 | 11/2011 | Vian et al. | |
| 8,294,899 B2 | 10/2012 | Wong | |
| 8,451,120 B2 | 5/2013 | Johnson, Jr. et al. | |
| 8,730,461 B2 | 5/2014 | Andreussi | |
| 9,183,371 B2 | 11/2015 | Narendra et al. | |
| 9,183,731 B1 | 11/2015 | Bokhary | |
| 9,235,974 B2 | 1/2016 | Johnson, Jr. et al. | |
| 9,250,175 B1 | 2/2016 | McManus | |
| 9,494,511 B2 * | 11/2016 | Wilkins ................ | G01J 3/0264 |
| 9,599,529 B1 | 3/2017 | Steele et al. | |
| 9,599,597 B1 | 3/2017 | Steele et al. | |
| 10,023,311 B2 | 7/2018 | Lai et al. | |
| 10,023,323 B1 | 7/2018 | Roberts et al. | |
| 10,031,040 B1 | 7/2018 | Smith et al. | |
| 10,126,200 B1 | 11/2018 | Steele et al. | |
| 10,268,198 B2 | 4/2019 | Mantripragada et al. | |
| 10,325,485 B1 | 6/2019 | Schuster | |
| 10,365,646 B1 | 7/2019 | Farnsworth et al. | |
| 10,429,546 B1 | 10/2019 | Ulmer | |
| 10,677,771 B2 | 6/2020 | Dittberner et al. | |
| 10,753,864 B2 | 8/2020 | Kasten et al. | |
| 10,816,458 B2 | 10/2020 | Kasten et al. | |
| 10,830,034 B2 | 11/2020 | Cooley et al. | |
| 10,962,437 B1 | 3/2021 | Nottrott et al. | |
| 11,105,784 B2 | 8/2021 | Kukreja et al. | |
| 11,112,308 B2 | 9/2021 | Kreitinger et al. | |
| 11,275,068 B2 | 3/2022 | Willett | |
| 11,299,268 B2 | 4/2022 | Christensen et al. | |
| 11,519,855 B2 | 12/2022 | Black et al. | |
| 11,557,212 B2 | 1/2023 | Hong | |
| 11,614,430 B2 | 3/2023 | Buckingham et al. | |
| 11,619,562 B2 | 4/2023 | Leen et al. | |
| 11,710,411 B2 | 7/2023 | Van Meeteren et al. | |
| 11,748,866 B2 | 9/2023 | Vargas | |
| 12,015,386 B2 | 6/2024 | Gatabi et al. | |
| 2002/0005955 A1 | 1/2002 | Kramer et al. | |
| 2003/0160174 A1 | 8/2003 | Grant et al. | |
| 2003/0189711 A1 | 10/2003 | Orr et al. | |
| 2003/0230716 A1 | 12/2003 | Russell et al. | |
| 2004/0012787 A1 | 1/2004 | Galle et al. | |
| 2004/0017762 A1 | 1/2004 | Sogawa et al. | |
| 2004/0212804 A1 | 10/2004 | Neff et al. | |
| 2006/0015290 A1 | 1/2006 | Warburton et al. | |
| 2006/0044562 A1 | 3/2006 | Hagene et al. | |
| 2006/0232772 A1 | 10/2006 | Silver | |
| 2006/0234621 A1 | 10/2006 | Desrochers et al. | |
| 2007/0137318 A1 | 6/2007 | Desrochers et al. | |
| 2008/0169934 A1 | 7/2008 | Lang et al. | |
| 2008/0243372 A1 | 10/2008 | Bodin et al. | |
| 2009/0201507 A1 | 8/2009 | Kluczynski et al. | |
| 2009/0263286 A1 | 10/2009 | Isomura et al. | |
| 2009/0326792 A1 | 12/2009 | McGrath | |
| 2010/0004798 A1 | 1/2010 | Bodin et al. | |
| 2010/0131207 A1 | 5/2010 | Lippert et al. | |
| 2010/0140478 A1 | 6/2010 | Wilson et al. | |
| 2010/0147081 A1 | 6/2010 | Thomas | |
| 2011/0035149 A1 | 2/2011 | McAndrew et al. | |
| 2011/0074476 A1 | 3/2011 | Heer et al. | |
| 2011/0150035 A1 | 6/2011 | Hanson et al. | |
| 2011/0164251 A1 | 7/2011 | Richter | |
| 2011/0213554 A1 | 9/2011 | Archibald et al. | |
| 2011/0242659 A1 | 10/2011 | Eckles et al. | |
| 2011/0257944 A1 | 10/2011 | Du et al. | |
| 2012/0120397 A1 | 5/2012 | Furtaw et al. | |
| 2013/0044314 A1 | 2/2013 | Koulikov et al. | |
| 2013/0076900 A1 | 3/2013 | Mrozek et al. | |
| 2013/0208262 A1 | 8/2013 | Andreussi | |
| 2014/0172323 A1 | 6/2014 | Marino | |
| 2014/0204382 A1 * | 7/2014 | Christensen ........ | G01N 21/3504 |
| | | | 356/402 |
| 2014/0236390 A1 | 11/2014 | Mohamadi | |
| 2014/0336957 A1 | 11/2014 | Hanson et al. | |
| 2015/0072633 A1 | 3/2015 | Massarella et al. | |
| 2015/0145954 A1 | 5/2015 | Pulleti et al. | |
| 2015/0226575 A1 | 8/2015 | Rambo | |
| 2015/0275114 A1 | 10/2015 | Tumiatti et al. | |
| 2015/0295543 A1 | 10/2015 | Brown et al. | |
| 2015/0316473 A1 | 11/2015 | Kester et al. | |
| 2015/0323449 A1 | 11/2015 | Jones et al. | |
| 2015/0336667 A1 | 11/2015 | Srivastava et al. | |
| 2016/0018373 A1 | 1/2016 | Pagé et al. | |
| 2016/0070265 A1 | 3/2016 | Liu et al. | |
| 2016/0104250 A1 | 4/2016 | Allen et al. | |
| 2016/0146696 A1 | 5/2016 | Steele et al. | |
| 2016/0161456 A1 | 6/2016 | Risk et al. | |
| 2016/0202225 A1 | 7/2016 | Feng et al. | |
| 2016/0214715 A1 | 7/2016 | Meffert | |
| 2016/0307447 A1 | 10/2016 | Johnson et al. | |
| 2016/0357192 A1 * | 12/2016 | McGrew ................ | B64U 10/25 |
| 2017/0003684 A1 | 1/2017 | Knudsen et al. | |
| 2017/0057081 A1 | 3/2017 | Krohne et al. | |
| 2017/0089829 A1 | 3/2017 | Bartholomew et al. | |
| 2017/0093122 A1 | 3/2017 | Bean et al. | |
| 2017/0097274 A1 | 4/2017 | Thorpe et al. | |
| 2017/0115218 A1 | 4/2017 | Huang et al. | |
| 2017/0134497 A1 | 5/2017 | Harter et al. | |
| 2017/0158353 A1 | 6/2017 | Schmick | |
| 2017/0199647 A1 | 7/2017 | Richman et al. | |
| 2017/0206648 A1 | 7/2017 | Marra et al. | |
| 2017/0235018 A1 | 8/2017 | Foster et al. | |
| 2017/0259920 A1 | 9/2017 | Lai et al. | |
| 2017/0290034 A1 | 10/2017 | Desai et al. | |
| 2017/0307519 A1 | 10/2017 | Black et al. | |
| 2017/0336281 A1 | 11/2017 | Waxman et al. | |
| 2017/0339820 A1 | 11/2017 | Foster et al. | |
| 2018/0023974 A1 | 1/2018 | Otani et al. | |
| 2018/0024091 A1 | 1/2018 | Wang et al. | |
| 2018/0045561 A1 | 2/2018 | Leen et al. | |
| 2018/0045596 A1 | 2/2018 | Prasad et al. | |
| 2018/0050798 A1 | 2/2018 | Kapuria | |
| 2018/0059003 A1 | 3/2018 | Jourdainne et al. | |
| 2018/0067066 A1 | 3/2018 | Giedd et al. | |
| 2018/0109767 A1 | 4/2018 | Li et al. | |
| 2018/0122246 A1 | 5/2018 | Clark | |

(56) References Cited

U.S. PATENT DOCUMENTS

| | | |
|---|---|---|
| 2018/0127093 A1 | 5/2018 | Christensen et al. |
| 2018/0188129 A1 | 7/2018 | Choudhury et al. |
| 2018/0209902 A1* | 7/2018 | Myshak .............. G01N 21/39 |
| 2018/0259955 A1 | 9/2018 | Noto |
| 2018/0266241 A1 | 9/2018 | Ferguson et al. |
| 2018/0266946 A1 | 9/2018 | Kotidis et al. |
| 2018/0284088 A1 | 10/2018 | Verbeck, IV |
| 2018/0292374 A1 | 10/2018 | Dittberner et al. |
| 2018/0321692 A1 | 11/2018 | Castillo-Effen et al. |
| 2018/0322699 A1 | 11/2018 | Gray et al. |
| 2019/0011920 A1 | 1/2019 | Heinonen et al. |
| 2019/0011935 A1 | 1/2019 | Ham et al. |
| 2019/0025199 A1 | 1/2019 | Koulikov |
| 2019/0033194 A1 | 1/2019 | DeFreez et al. |
| 2019/0049364 A1 | 2/2019 | Rubin |
| 2019/0077506 A1 | 3/2019 | Shaw et al. |
| 2019/0086202 A1 | 3/2019 | Guan et al. |
| 2019/0095687 A1 | 3/2019 | Shaw et al. |
| 2019/0154874 A1 | 5/2019 | Shams et al. |
| 2019/0178743 A1 | 6/2019 | McNeil |
| 2019/0195789 A1 | 6/2019 | Pan et al. |
| 2019/0204189 A1 | 7/2019 | Mohr, Jr. et al. |
| 2019/0212419 A1 | 7/2019 | Jeong et al. |
| 2019/0220019 A1 | 7/2019 | Tan et al. |
| 2019/0228573 A1 | 7/2019 | Sen et al. |
| 2019/0234868 A1 | 8/2019 | Tanomura et al. |
| 2019/0331652 A1 | 10/2019 | Ba et al. |
| 2020/0050189 A1 | 2/2020 | Gu et al. |
| 2020/0065433 A1 | 2/2020 | Duff et al. |
| 2020/0109976 A1 | 4/2020 | Ajay et al. |
| 2020/0135036 A1 | 4/2020 | Campbell |
| 2020/0182779 A1 | 6/2020 | Kasten et al. |
| 2020/0249092 A1 | 8/2020 | Podmore et al. |
| 2020/0373172 A1 | 11/2020 | Suzuki |
| 2020/0400635 A1 | 12/2020 | Potyrailo et al. |
| 2021/0017926 A1 | 1/2021 | Alkadi et al. |
| 2021/0037197 A1 | 2/2021 | Kester et al. |
| 2021/0055180 A1 | 2/2021 | Thorpe et al. |
| 2021/0109074 A1 | 4/2021 | Smith et al. |
| 2021/0140934 A1 | 5/2021 | Smith et al. |
| 2021/0190745 A1 | 6/2021 | Buckingham et al. |
| 2021/0190918 A1 | 6/2021 | Li et al. |
| 2021/0199565 A1 | 7/2021 | John et al. |
| 2021/0247369 A1 | 8/2021 | Nottrott et al. |
| 2021/0255158 A1 | 8/2021 | Smith et al. |
| 2021/0300591 A1 | 9/2021 | Tian |
| 2021/0321174 A1 | 10/2021 | Sun et al. |
| 2021/0364427 A1 | 11/2021 | Smith et al. |
| 2021/0382475 A1 | 12/2021 | Smith et al. |
| 2022/0082495 A1 | 3/2022 | Kreitinger et al. |
| 2022/0113290 A1 | 4/2022 | Smith et al. |
| 2022/0170810 A1 | 6/2022 | Miller, II et al. |
| 2022/0268952 A1 | 8/2022 | Liang et al. |
| 2022/0341806 A1 | 10/2022 | Miller et al. |
| 2022/0357231 A1 | 11/2022 | Nahata et al. |
| 2023/0194487 A1 | 6/2023 | Buckingham et al. |
| 2023/0213413 A1 | 7/2023 | Mohr, Jr. et al. |
| 2023/0274651 A1 | 8/2023 | McGuire et al. |
| 2023/0392498 A1 | 12/2023 | Srivastav et al. |

FOREIGN PATENT DOCUMENTS

| | | |
|---|---|---|
| CN | 104458588 A | 3/2015 |
| CN | 205749271 U | 11/2016 |
| CN | 106568516 A | 4/2017 |
| CN | 106769977 A | 5/2017 |
| CN | 107703075 A | 2/2018 |
| CN | 109780452 A | 5/2019 |
| CN | 211508182 U | 9/2020 |
| CN | 112213443 A | 1/2021 |
| DE | 29601472 U1 | 5/1996 |
| DE | 69333010 | 4/2004 |
| DE | 102014013822 A1 | 3/2016 |
| EP | 0450809 A2 | 10/1991 |
| EP | 1371962 B1 | 7/2011 |
| EP | 3339855 A1 | 6/2018 |
| FR | 3047073 A1 | 7/2017 |
| FR | 3047073 B1 | 8/2019 |
| GB | 2538563 A | 11/2016 |
| JP | H08247939 A | 9/1996 |
| JP | 200975823 A | 4/2009 |
| KR | 20170062813 A | 6/2017 |
| KR | 101770254 B1 | 8/2017 |
| TW | 522226 B | 3/2003 |
| WO | 1999054700 A2 | 10/1999 |
| WO | 02066950 A1 | 8/2002 |
| WO | 2008021311 A2 | 2/2008 |
| WO | 2015073687 A1 | 5/2015 |
| WO | 2016045791 A1 | 3/2016 |
| WO | 2016/162673 A1 | 10/2016 |
| WO | 2017069979 A1 | 4/2017 |
| WO | 2018121478 A1 | 7/2018 |
| WO | 2018227153 A1 | 12/2018 |
| WO | 2019246280 A1 | 12/2019 |
| WO | 2020007684 A1 | 1/2020 |
| WO | 2020028353 A1 | 2/2020 |
| WO | 2020086499 A1 | 4/2020 |
| WO | 2020206006 A1 | 10/2020 |
| WO | 2020206008 A1 | 10/2020 |
| WO | 2020206020 A1 | 10/2020 |
| WO | 2021055902 A1 | 3/2021 |
| WO | 2021158916 A1 | 8/2021 |
| WO | 2022093864 A1 | 5/2022 |
| WO | 2022211837 A1 | 10/2022 |

OTHER PUBLICATIONS

Lilian Joly, The evolution of AMULSE (Atmospheric Measurements by Ultra-Light Spectrometer) and its interest in atmospheric applications. Results of the Atmospheric Profiles of Greenhouse gasEs (APOGEE) weather balloon release campaign for satellite retrieval validation, p. 1-28, Sep. 25, 2019, Atmospheric Measurement Techniques Discussion (Joly).

International Search Report and Written Opinion for PCT/US2023/023933 mailed Sep. 26, 2023.

IEEE Conference Paper, "Research of the high pressure jet performance of small size nozzle," ISBN :978-1-5090-1087-5, Publication Date : Oct. 1, 2016, Conference dates Oct. 10, 2016 thru Oct. 12, 2016.[retrieved from the Internet] on Sep. 1, 2023 at 4:14pm.

Clilverd, Mark A. et al., Energetic particle injection, acceleration, and loss during the geomagnetic disturbances which upset Galaxy 15, Journal of Geophysical Research, vol. 117, A12213, doi: 10.1029/2012JA018175, 2012, pp. 1-16 (Year:2012).

Kern, Christoph et al., Spatial Distribution of Halogen Oxides in the Plume of Mount Pagan Volcano, Mariana Islands, Geophysical Research Letters 10.1029/2018GL079245, Sep. 27, 2018, pp. 9588-9596 (Year:2018).

Liao, J. et al. Observations of Inorganic bromine(HOBr, BrO, and Br2) speciation at Barrow, Alaska in spring 2009, Journal of Geophysical Research, vol. 117, D00R16, doi:10.1029/2011JD016641, 2012, pp. 1-11 (Year:2012).

Liu, Siwen et al., Development of a UAV-Based System to Monitor Air Quality over an Oil Field, Montana Technological University, Montana tech Library Digital Commons @ Montana Tech Graduate Theses & Non-Theses, Fall 2018, pp. 1-85 (Year:2018).

Miyama, Toru et al., Estimating allowable carbon emission for CO2 concentration stabilization using a GCM-based Earth system model, Geophysical Research Letters, vol. 36,L19709, doi:10.1029/2009GL039678, 2009, pp. 0094-8276 (Year:2009).

Oppenheimer Clive et al., Ultraviolet Sensing of Volcanic Sulfur Emissions, Elements (An Internatioknal Magazine of Mineralogy, Geochemistry, and Petrology), Apr. 2010, vol. 6, pp. 87-92 (Year: 2010).

Parazoo, Nicholas C. et al., Interpreting seasonal changes in the carbon balance of southern Amazonia using measurements of XCO2 and chlorophyll fluorescence from Gosat, Geophysical Research Letters, vol. 40.2829-2833, doi: 10.1002/grl.50452, 2013 pp. 0 2829-2833 (Year:2013).

(56) References Cited

OTHER PUBLICATIONS

Queiber, Manuel et al., A new frontier in CO2 flux measurements using a highly portable Dial laser system, Scientific Reports, DOI: 10.1038/srep33834 1, Sep. 22, 2016, pp. 1-13(Year:2016).

Queiber, Manuel et al., Large-area quantification of subaerial CO2 anomalies with portable laser remote sensing and 2d tomography, The Leading Edge Mar. 2018, pp. 306-313 (Year:2018).

International Search Report and Written Opinion for PCT/US22/38951, mailed Nov. 28, 2022.

Kelly J F et al. "A capillary absorption spectrometer for stable carbon isotope ratio (C/C) analysis in very small samples", Review of Scientific Instruments, American Institute of Physics, 2 Huntington Quadrangle, Melville, NY 11747, vol. 83, No. 2, Feb. 1, 2012 (Feb. 1, 2012), pp. 23101-23101, XP012161835, ISSN: 0034-6748, DOI: 10.1063/1.3680593.

Krings et al., Atmos. Meas. Tech., 11, 721-739, Feb. 7, 2018.

Khan et al., "Low Power Greenhouse Gas Sensors for Unmanned Aerial Vehicles," Remote Sens. 2012, 4, 1355-1368; doi: 10.3390/rs4051355 [retrieved on Dec. 6, 2019]. Retrieved from the internet: <URL: https://www.cfa.harvard.edu/~kangsun/files/Khan_Low%20Power%20Greenhouse%20Gas%20Sensors%20for%20Unmanned%20Aerial%20Vehicles.pdf> pp. 1-14.

Joly et al. "Atmospheric Measurements by Ultra-Light Spectrometer (AMULSE) Dedicated to Vertical Profile in Situ Measurements of Carbon Dioxide (CO2) Under Weather Balloons: Instrumental Development and Field Application," Sensors 2016, 16, 1609; doi: 10.3390/s 16101609 www.mdpi.com/journal/sensors, [retrieved on Dec. 6, 2019]. Retrieved from the internet: <URL: https://www.ncbi.nlm.nih.gov/pmc/articles/PMC5087397/pdf/sensors-16-01609.pdf> pp. 1-14.

White et al. "Development of an Unmanned Aerial Vehicle for the Measurement of Turbulance in the Atmospheric Boundary Layer," Published in Atmosphere v. 8, issue 10, 195, p. 1-25. [retrieved on Dec. 6, 2019]. Retrieved from the Internet: <URL: https://uknowledge.uky.edu/cgi/viewcontent.cgi?article=1033&context=me_facpub> pp. 1-27.

International Search Report and Written opinion for PCT/US19/57305 mailed Jan. 2, 2020.

"Safesite Multi-Threat Detection System", Jul. 11, 2012 (Jul. 11, 2012), pp. 1-6, XP055245980.

International Search Report and Written Opinion for PCT/US19/38011 mailed Sep. 9, 2019.

International Search Report and Written Opinion for PCT/US19/38015, mailed Oct. 18, 2019.

International Search Report and Written Opinion for PCT/US19/44119, mailed Oct. 17, 2019.

International Search Report and Written Opinion for PCT/US20/26228 mailed Jul. 1, 2020.

International Search Report and Written Opinion for PCT/US20/26232 mailed Jun. 26, 2020.

International Search Report and Written Opinion for PCT/US20/26246 mailed Jun. 29, 2020.

International Search Report and Written Opinion for PCT/US20/51696, mailed Feb. 3, 2021.

International Search Report and Written Opinion for PCT/US2020/044978, mailed Oct. 26, 2020.

International Search Report and Written Opinion for PCT/US2021/016821 mailed Apr. 26, 2021.

International Search Report and Written Opinion for PCT/US2021/024177, mailed Jun. 23, 2021.

International Search Report and Written Opinion for PCT/US2021/056708, mailed Jan. 27, 2022.

International Search Report and Written Opinion for PCT/US21/42061, mailed Nov. 26, 2021.

International Search Report and Written Opinion for PCT/US21/44532, mailed Jan. 11, 2022.

International Search Report and Written Opinion for PCT/US21/56710, mailed Feb. 23, 2022.

International Search Report and Written Opinion of PCT/US19/57305, mailed Jan. 2, 2020.

International Search Report and Written Opinion of PCT/US20/54117, mailed Dec. 22, 2020.

Joly, "Atmospheric Measurements by Ultra-Light Spectrometer (AMULSE) Dedicated to Vertical Profile In Situ Measurements of Carbon Dioxide (CO2) Under Weather Balloons: Instrumental Development and Field Application," Sensors 2016, 16, 1609.

Khan, "Low Power Greenhouse Gas Sensors for Unmanned Aerial Vehicles", Remote Snse. 2012, 4, 1355-1368.

Villa. "An Overview of Small Unmanned Aerial Vehicles for Air Quality Measurements: Present Applications and Future Prospectives". Sensors. Web . Jul. 12, 2016.

White, "Development of an Unmanned Aerial Vehicle for the Measurement of Turbulence in the Atmospheric Boundary Layer", Atmosphere, v.8, issue 10, 195, pp. 1-25.

International Search Report and Written Opinion for PCT/US23/23905 mailed Oct. 5, 2023.

Development of a mobile tracer correlation method for assessment of air emissions from landfills and other area sources, Atmospheric Environment 102 (2015) 323-330. T.A. Foster-Wittig et al. 2015.

Measurements of Methane Emissions from Landfills Using a Time Correlation Tracer Method Based on FTIR Absorption Spectroscopy, Environ. Sci. Technol. 2001, 35, 21-25, B. Galle et al. 2001.

Uehara, K: "Dependence of harmonic signals 1-15 on sample-gas parameters in wavelength-modulation spectroscopy for precise absorption measurements", Applied Physics B, Springer Berlin Heidelberg, Berlin/Heidelberg, vol. 67, Jan. 2, 1998, pp. 517-523, XP007921671, ISSN:0946-2171, DOI: 10.1007/S003400050537.

Field Trial of Methane Emission Quantification Technologies, Society of Petroleum Engineers, SPE-201537-MS, Allen et al., Oct. 2020.

Feng, Lingbing, Nowak, Gen, O'Neill, T.J., Welsh, A.H."Cutoff; A spatio-temporal imputation method." Journal of Hydrology 519 (2014) : 3591-3605 (Year:2014).

Cabreira et al. "Survey on Coverage Path Planning with Unmanned Aerial Vehicles", published: Drones, published: Jan. 2019, pp. 1-38, year 2019.

Tao Lei et al:"Low-power, open-path mobile sensing platform for high-resolution measurements of greenhouse gases and air pollutants", Applied Physics B, Springer Berlin Heidelberg, Berlin/Heidelberg, vol. 119, No. 1, Mar. 10, 2015 (Mar. 10, 2015), pp. 153.-164, XP035445836, ISSN: 0946-2171, DOI: 10.1007/S00340-015-6069-1 [retrieved on Mar. 10, 2015].

Tarsitano C G et al: Multilaser Herriott Cell for Planetary Tunable Laser Spectrometers', Applied Optics , Optical Society of America, Washington, DC, US, vol. 46, No. 28, Oct. 1, 2007 (Oct. 1, 2007), pp. 6923-6935, XP001508502, ISSN:0003-6935, DOI: 10.1364/AO.46.006923.

Adame J A et al: "Application of cluster analysis to surface ozone, NOand SOdaily patterns in an industrial area in Central-Southern Spain measured with a DOAS system", Science of The Total Environment, Elsevier, Amsterdam, NL, vol. 429, Apr. 11, 2012 (Apr. 11, 2012), pp. 281-291, XP028491183, ISSN: 0048-9697, DOI: 10.1016/J.SCITOTENV.2012.04.032.

Coombes et al, "Optimal Polygon Decomposition for UAV Survey Coverage Path Planning in Wind", published: Jul. 2018, publisher: 'Sensors' (Year:2018).

He et al. "Static Targets' Track Path for UAVs Meeting the Revisit Interval Requirement", published :2013, publisher : IEEE (Year:2013).

Day, S., and et al. "Characterisation of regional fluxes of methane in the Surat Basin, Queensland, Phase 1: A review and analysis of literature on methane detection and flux determination." (2013) (Year: 2013).

\* cited by examiner

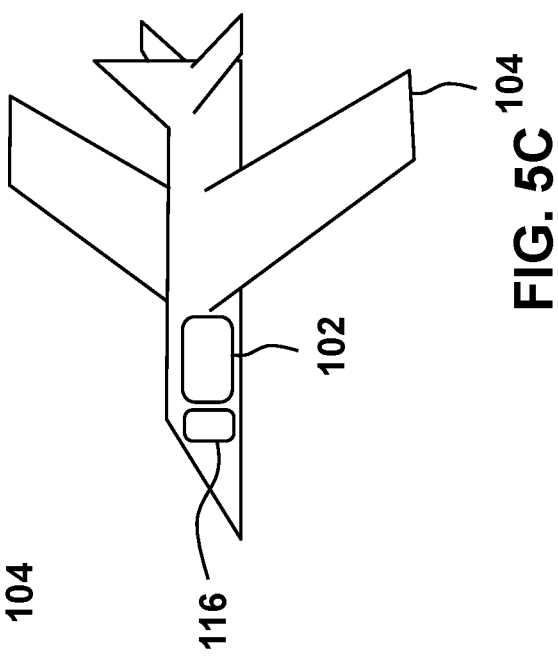
FIG. 5B
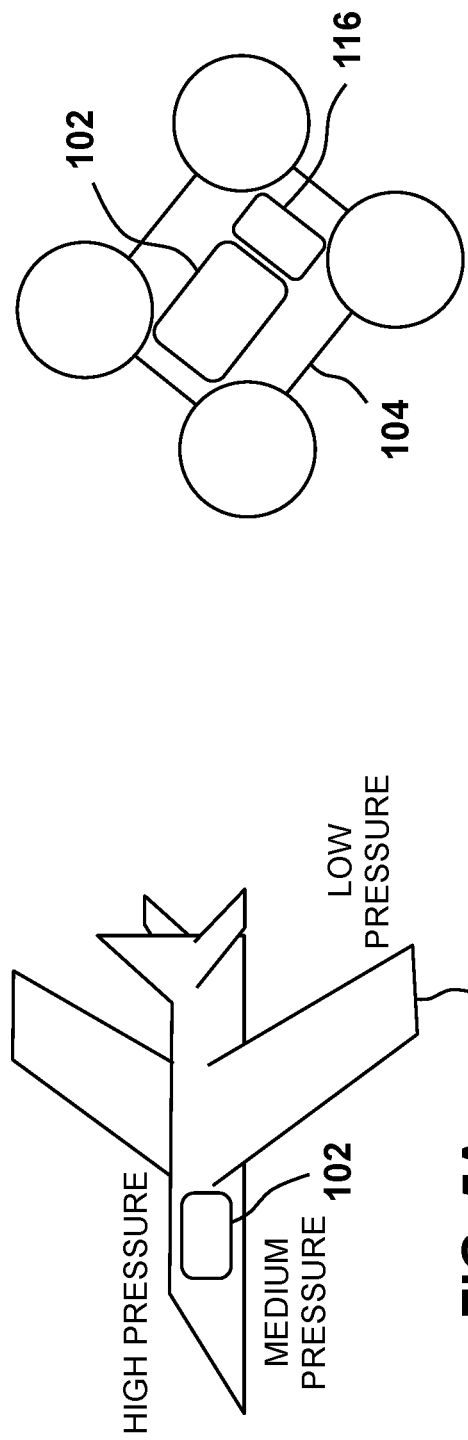
FIG. 5C
FIG. 5A

UAV-BORNE, HIGH-BANDWIDTH, LIGHTWEIGHT POINT SENSOR FOR QUANTIFYING GREENHOUSE GASES IN ATMOSPHERIC STRATA

This application is a 35 U.S.C § 371 National Stage Entry of International Application No. PCT/US2019/057305, filed Oct. 22, 2019, which claims the priority benefit of U.S. Provisional Patent Application Ser. No. 62/748,647, filed Oct. 22, 2018, all of which are incorporated herein by reference in their entirety for all purposes.

FIELD OF ENDEAVOR

The invention relates to gas detection, and more particularly to sensor-based gas detection.

BACKGROUND

Methane ($CH_4$) is an odorless and colorless naturally occurring organic molecule, which is present in the atmosphere at average ambient levels of approximately 1.85 ppm as of 2018 and is projected to continually climb. Methane is a powerful greenhouse gas, a source of energy (i.e., methane is flammable), and an explosion hazard, and so detection of methane is of utility to scientists as well as engineers. While methane is found globally in the atmosphere, a significant amount is collected or "produced" through anthropogenic processes including exploration, extraction, and distribution of petroleum resources as a component in natural gas. Natural gas, an odorless and colorless gas, is a primary fuel used to produce electricity and heat. The main component of natural gas is typically methane, and the concentration of methane in a stream of natural gas can range from about 70% to 90%. The balance of the gas mixture in natural gas consists of longer chain hydrocarbons, including ethane, propane, and butane, typically found in diminishing mole fractions that depend on the geology of the earth from which the gas is extracted. Once extracted from the ground, natural gas is processed into a product that must comply with specifications for both transport, taxation, and end-use in burners; specification of processed 'downstream' natural gas product control for the composition of the gas, so as to protect transport lines from corrosion and ensure proper operation of burners and turbines. While extraction of natural gas is one of the main sources of methane in the atmosphere, major contributors of methane also include livestock farming (i.e., enteric fermentation) and solid waste and wastewater treatment (i.e., anaerobic digestion). Anaerobic digestion and enteric fermentation gas products consist primarily of methane and lack additional hydrocarbon species.

SUMMARY

A system embodiment may include: a gas sensor comprising one or more optical cells; a processor having addressable memory, the processor configured to: detect gas from the one or more optical cells of the gas sensor, where the detected gas may be one or more of: methane, carbon dioxide, hydrogen sulfide, water, ammonia, sulfur oxides, and nitrogen; record data corresponding to the detected gas, where the recorded data comprises at least one of: an ambient temperature from a temperature sensor, an ambient pressure from a pressure sensor, an aerial vehicle telemetry, and an aerial vehicle location from a global positioning system (GPS); and generate a map of atmospheric greenhouse gas concentration on a map based on the detected gas and the recorded data.

Additional system embodiments may include: a gas handling system configured to supply atmospheric gas to the gas sensor. In additional system embodiments, the gas handling system may comprise at least one of: a pump, a ram-air design, and a velocity-induced vacuum. Additional system embodiments may include: a thermal chamber configured to modify a temperature of the supplied atmospheric gas to a set temperature. Additional system embodiments may include: a pressure regulator configured to modify a pressure of the supplied atmospheric gas to a set pressure.

In additional system embodiments, the processor may be further configured to: actively adjust at least one operating parameter of the gas sensor based on the recorded data. In additional system embodiments, the at least one operating parameter of the gas sensor may be an acquisition rate. In additional system embodiments, the acquisition rate may be increased by the processor based on an increased speed of an aerial vehicle from the recorded data of the aerial vehicle location to maintain a substantially constant spatial distribution of sampled locations. In additional system embodiments, the acquisition rate may be increased by the processor based on an aerial vehicle traversing an area with increased turbulence based on the recorded data.

Additional system embodiments may include: an aerial vehicle, where the gas sensor is mounted on the aerial vehicle. In additional system embodiments, the aerial vehicle may be an unmanned aerial vehicle (UAV). In additional system embodiments, the gas sensor may be mounted in a fuselage of the aerial vehicle. In additional system embodiments, the gas sensor may be mounted distal from a fuselage of the aerial vehicle.

Additional system embodiments may include: a ground control station (GCS) in communication with the gas sensor, the GCS comprising a GCS processor having addressable memory, the GCS processor configured to: receive the detected gas from the one or more optical cells of the gas sensor; receive the recorded data corresponding to the detected gas; and provide instructions to the aerial vehicle to follow a flight path. Additional system embodiments may include: a power management and laser control logic system configured to supply a laser of each of the one or more optical cells with a drive current, an operating temperature, and a power consumption within operating bounds of each laser.

A method embodiment may include: providing an atmospheric gas to a gas sensor; detecting, by one or more optical cells of the gas sensor, gas from one or more of: methane, carbon dioxide, water, hydrogen sulfide, ammonia, sulfur oxides, and nitrogen oxides; recording, by a processor having addressable memory, data corresponding to the detected gas from at least one of: an ambient temperature, an ambient pressure, an aerial vehicle telemetry, and an aerial vehicle location; and generating, by the processor, an atmospheric greenhouse gas concentration data on a map based on the detected gas and recorded data.

Additional method embodiments may include: receiving atmospheric gas from a gas handling system. Additional method embodiments may include, prior to providing the atmospheric gas to the gas sensor: measuring or inferring a temperature of the received atmospheric gas from the gas handling system; and modifying the temperature of the received atmospheric gas to a set temperature via a thermal chamber. Additional method embodiments may include, prior to providing the atmospheric gas to the gas sensor:

measuring or inferring a pressure of the received atmospheric gas from the gas handling system; and modifying the pressure of the received atmospheric gas to a set pressure via a pressure regulator.

Another system embodiment may include: an unmanned aerial vehicle (UAV); a gas handling system configured to supply atmospheric gas to a gas sensor; a thermal chamber configured to modify a temperature of the supplied atmospheric gas to a set temperature; a pressure regulator configured to modify a pressure of the supplied atmospheric gas to a set pressure; one or more optical cells of the gas sensor, where the gas sensor may be mounted to the UAV; a processor having addressable memory, the processor configured to: detect gas from the one or more optical cells of the gas sensor, where the detected gas may be one or more of: methane, carbon dioxide, hydrogen sulfide, water, ammonia, sulfur oxides, and nitrogen; record data corresponding to the detected gas, where the recorded data comprises at least one of: an ambient temperature from a temperature sensor, an ambient pressure from a pressure sensor, an aerial vehicle telemetry, and an aerial vehicle location from a global positioning system (GPS); actively adjust at least one operating parameter of the gas sensor based on the recorded data; and generate a map of atmospheric greenhouse gas concentration on a map based on the detected gas and the recorded data.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 5A depicts a gas sensor mounted on an aerial vehicle and receiving gas samples from relatively high pressure zones to relatively low pressure zones, according to one embodiment;

FIG. 5B depicts a gas sensor mounted on a quadcopter UAV and receiving gas samples from a gas handling system, according to one embodiment;

FIG. 5C depicts a gas sensor mounted on an aerial vehicle and receiving gas samples from a gas handling system where elative pressure differentials may be inconsistent given a prescribed flight envelope, according to one embodiment;

DETAILED DESCRIPTION

The following description is made for the purpose of illustrating the general principles of the embodiments discloses herein and is not meant to limit the concepts disclosed herein. Further, particular features described herein can be used in combination with other described features in each of the various possible combinations and permutations. Unless otherwise specifically defined herein, all terms are to be given their broadest possible interpretation including meanings implied from the description as well as meanings understood by those skilled in the art and/or as defined in dictionaries, treatises, etc.

The present system allows for a gas sensor attached to an aerial vehicle, such as an unmanned aerial vehicle (UAV), to quantify gas concentrations at specific locations and times in locales that may be inaccessible by manned aircraft and/or risky flight environments. The disclosed greenhouse gas sensor may be flown as a payload on an airborne platform, such as a UAV, to take these measurements and acquire point concentration measurements of $CO_2$, $CH_4$, and/or $H_2O$ (gas) while in flight. The disclosed sensor provides a light sensor weight, resilience to temperature and pressure changes, operates with sufficient sampling rate, and complies with electrical power limits.

Figure 1:
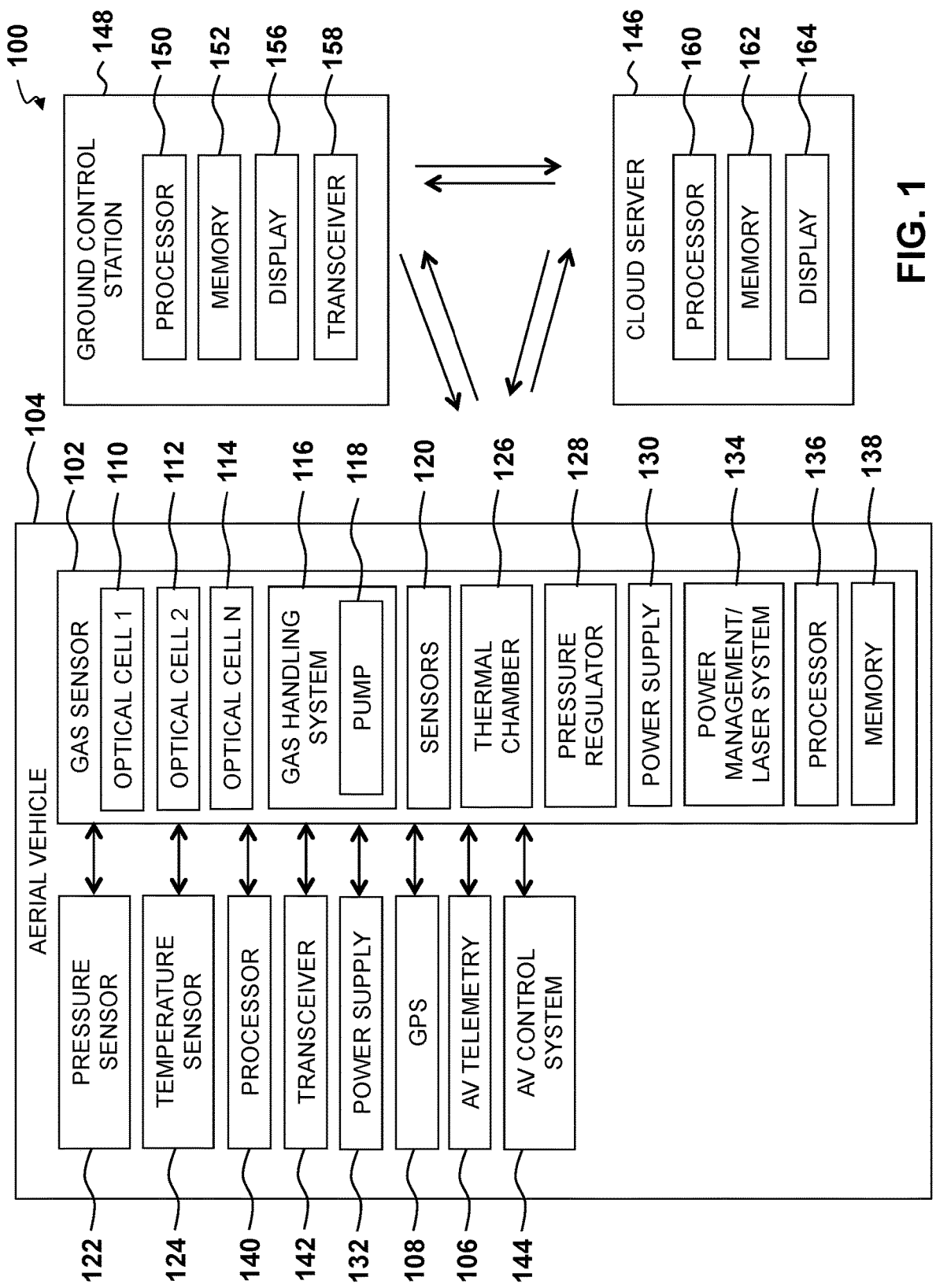
FIG. 1 depicts a high-level block diagram of a gas sensor system, according to one embodiment.

FIG. 1 depicts a high-level block diagram of a gas sensor system 100, according to one embodiment. Trace gas sensing is of general interest for a wide variety of scientific and engineering analyses. Knowledge of specific gas concentration at a specific location can improve understanding of system performance and enable prediction of system dynamics. Carbon dioxide ($CO_2$), methane, $CH_4$, and/or water vapor ($H_2O$), are greenhouse gases, and their distribution throughout the strata of the atmosphere is of interest to meteorologists, industrial process designers, and scientists in their efforts to understand climate and the impact of anthropogenic industry on climate. The disclosed system 100 is able to localize and quantify greenhouse gas concentrations in the atmosphere. Remotely piloted or autonomous vehicles, i.e., unmanned airborne vehicles (UAVs), provide an opportunity to fly trace gas sensors capable of quantifying gas concentrations at a specific location and time in locales that are inaccessible by manned aircraft and/or in risky flight environments. The disclosed greenhouse gas sensor 102 may be flown as a payload on an aerial vehicle 104 to obtain these gas measurements where previously not available.

The airborne greenhouse gas sensor (GHGS) 102 may be carried as a payload on an airborne platform 104, and the GHGS 102 may acquire point concentration measurements of $CO_2$, $CH_4$, and/or $H_2O$ (gas) while in flight. The GHGS 102 may interface with UAV telemetry 106 and a global positioning system (GPS) 108 to localize gas measurements.

The GHGS 102 may be an ultra-lightweight, low power, part-per-billion (ppb) sensitivity, mid-Infrared (wavelength $\lambda=3-8$ μm), open path gas concentration sensor with sampling rate greater than or equal to 10 Hz; such a sensor infers gas concentration by measuring the absorption of laser light. In some embodiments, the GHGS 102 may weigh less than 1.4 kg. In some embodiments, the GHGS 102 may be tuned to detecting a single gas species. The single species may be methane, carbon dioxide, water, hydrogen sulfide, ammonia, sulfur oxides, or nitrogen oxides. In some embodiments, the GHGS 102 may be tuned to detect two or more different gas species, such as methane, carbon dioxide, water, hydrogen sulfide, ammonia, sulfur oxides, and/or nitrogen oxides. In some embodiments, a single optical cell 110 may be used. In other embodiments, multiple optical cells 110, 112, 114 may be used. Each optical cell 110, 112, 114 may contain a gas flow path, through which gas concentration may be interrogated for one or more species. In some embodiments, the one or more optical cells 110, 112, 114 may be open to the atmosphere. In other embodiments, the one or more optical cells 110, 112, 114 may be a closed system through which a gas sample flows through. Each optical cell 110, 112, 114 may provide a path for a laser beam to traverse. In some embodiments, the optical cell 110, 112, 114 may be a Herriott cell. In other embodiments, the optical cell 110, 112, 114 may be a high-finesse cavity. In other embodiments, the optical cell 110, 112, 114 may be a simple pitch-and-catch optical arrangement.

The system 100 may include a gas handling system 116 to deliver atmospheric air samples to the one or more optical cells 110, 112, 114. In some embodiments, the gas handling system 116 may use at least one pump 118. In other embodiments, the gas handling system 116 may use a ram-air design. In other embodiments, the gas handling system 116 may use velocity-induced vacuum. In some embodiments, the gas handling system 116 may use a combination of the pump 118, the ram-air design, and/or the velocity-induced vacuum.

Onboard sensors 120 may be used to determine ambient temperature and pressure in the GHGS 102 sensor head. In other embodiments, a pressure sensor 122 and/or a temperature sensor 124 of the aerial vehicle 104 may provide sensor measurements to the GHGS 102. In other embodiments, the ambient temperature and pressure in the GHGS 102 sensor head may be inferred from the measurements acquired in the optical cells 110, 112, 114.

In some embodiments, a thermal chamber 126 may be used to warm or cool atmospheric gas to a specific temperature before it reaches the GHGS 102 sensor head. In some embodiments, a pressure regulator 128 may be used to control the pressure of the gas sample in the GHGS 102 sensor head.

A power supply device 130 may be integrated into the GHGS 102 sensor head in some embodiments. In other embodiments, the power supply device 130 may be mounted remotely from the sensor payload and connected by cables to the sensor 102. A power supply 132 of the aerial vehicle 104 may be used to supply power to the sensor 102 in some embodiments. In some embodiments, the power supply 132 may be mounted elsewhere on the airframe of the aerial vehicle 104 and connected to the sensor 102 via cables.

A power management and laser control logic system 134 may be used to ensure that: lasers are supplied with drive current within the laser operating bounds, laser operating temperatures do not exceed laser operating bounds, and/or overall power consumption is within constraints specified by the aerial vehicle 104 payload specification. In some embodiments, heat ejected from the laser may be used to warm the thermal chamber 126.

A processor 136 and addressable memory 138 may contain the sensor 102 firmware and low-level data processing functions. In some embodiments, the processor 136 and/or addressable memory 138 may be mounted remotely from the sensor head and connected wirelessly or by cables to the sensor 102. In some embodiments, multiple processors may be used. In some embodiments, a processor 140 of the aerial vehicle 104 may be used with the sensor 102.

In some embodiments, the GPS 108 may be mounted remotely from the GHGS 102 sensor head and connected wirelessly or by cables to the processor 136 for positional data acquisition. A wireless radio or cellular connection, such as a transceiver 142, may provide remote uni- or bi-directional data transfer between the airborne sensor system and an AV telemetry system 106, an AV control system 144, a cloud server/processor 146, and/or a ground control station 148.

The aerial vehicle 104 and/or the sensor 102 may communicate with the ground control station 148. The ground control station may receive gas measurements from the gas sensor 102, location and sensor data from the aerial vehicle 104, and/or provide instructions to the aerial vehicle 104 to follow a flight path. The ground control station may include a processor 150, a memory 152, a display 156, and a transceiver 158. In some embodiments, the collected atmospheric greenhouse gas concentration data may be shown on a map on the display 156. This map may be a satellite image, aerial image, two-dimensional color map, two-dimensional contour map, and/or three-dimensional topographical surface/mesh map.

The aerial vehicle 104, the sensor 102, and/or the ground control station 148 may communicate with a cloud server 146. The cloud server 146 may include a processor 160, a memory 162, and/or a display 164. The aerial vehicle 104, sensor 102, ground control station 148, and/or cloud server 146 may perform additional processing on the readings of the gas sensor 102 combined with data on the aerial vehicle 104 location, pressure, temperature, time, and the like. Any components of the gas sensor 102 may be part of the aerial vehicle 104. The gas sensor 104 may receive measurements, data, and/or power from any components of the aerial vehicle 104.

The GCS 148 processor 150, gas sensor 102 processor 136, and/or aerial vehicle 104 processor 140 may control the gas sensor 102, interface with UAV telemetry, interface with the GCS 148, and/or adjust the gas sensor operating parameters, e.g., the sensor sampling rate, based on information collected from UAV telemetry or the ground control station. For example, the processor 150, 136, 140 may increase a gas sensor sampling rate to adjust for increased UAV speed so as to maintain a constant spatial distribution of sampled locations. As another example, the processor 150, 136, 140 may increase sampling rate if the computer infers that the UAV is traversing part of the atmosphere with relatively high turbulence.

Figure 2:
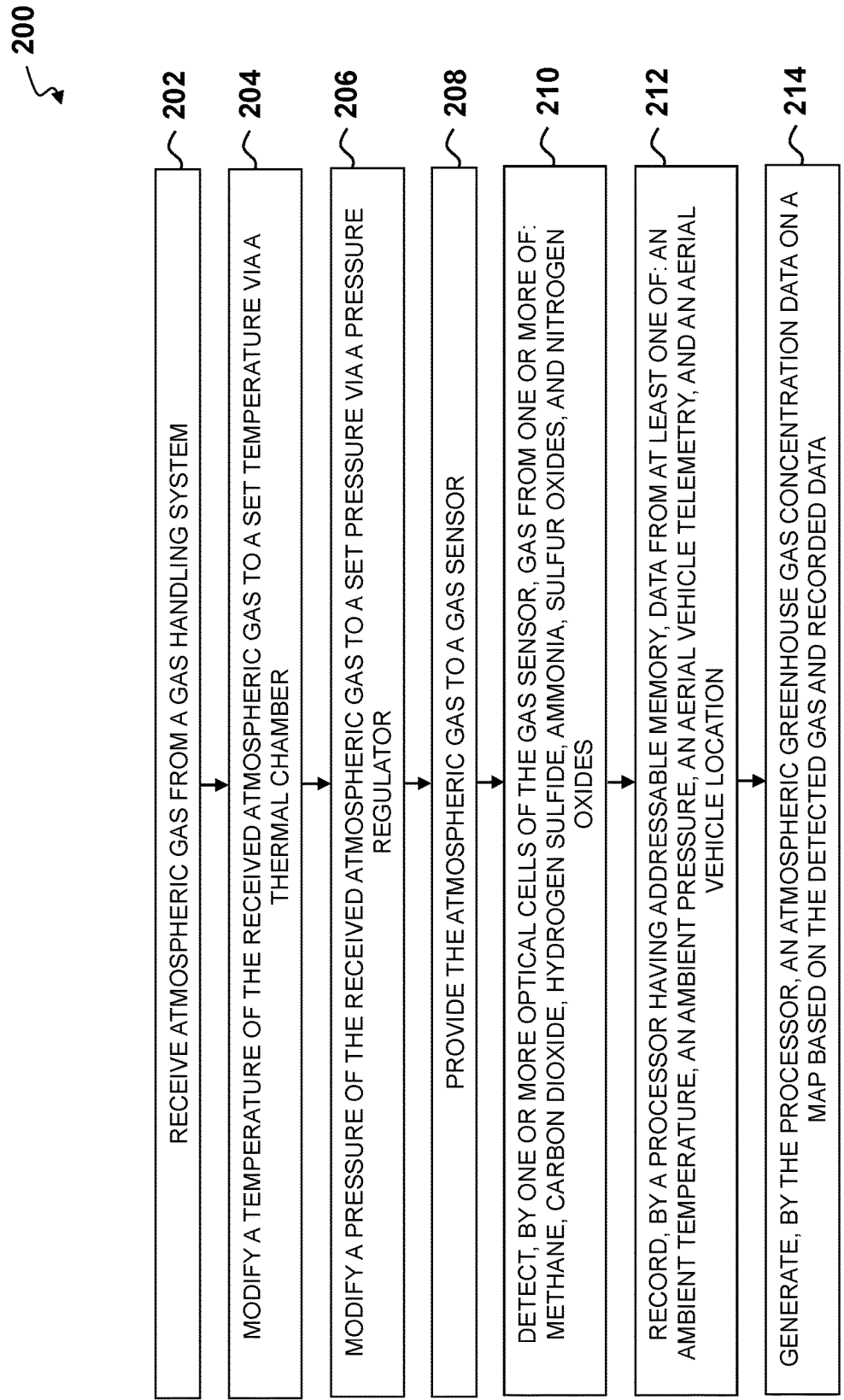
FIG. 2 depicts a high-level flowchart of a method embodiment of detecting gas via a payload attached to an unmanned aerial vehicle (UAV), according to one embodiment.

FIG. 2 depicts a high-level flowchart of a method embodiment 200 of detecting gas via a payload attached to an aerial vehicle such as an unmanned aerial vehicle (UAV), according to one embodiment. The method 200 may include receiving atmospheric gas from a gas handling system (step 202). The gas handling system may include a pump, a ram-air design, and/or a velocity-induced vacuum. In some embodiments, the gas sensor may be mounted in a payload in a location on an aerial vehicle such that the gas handling system is not needed. In some embodiments, the gas handling system may not be used and atmospheric gas may be directly input into the one or more optical cells of the sensor.

The method 200 may then include modifying a temperature of the received atmospheric gas to a set temperature via a thermal chamber (step 204). In some embodiments, the thermal chamber may increase the temperature of the atmospheric gas to the set temperature. In other embodiments, the thermal chamber may decrease the temperature of the atmospheric gas to the set temperature. In other embodiments, the thermal chamber may not be needed and the atmospheric gas may remain at an ambient temperature. The method 200 may then include modifying a pressure of the received atmospheric gas to a set pressure via a pressure regulator (step 206). In some embodiments, the pressure regulator may increase the pressure of the atmospheric gas to the set pressure. In other embodiments, the pressure regulator may decrease the pressure of the atmospheric gas to the set pressure. In some embodiments, the pressure regulator may not be needed and the pressure of the atmospheric gas may remain at an ambient pressure. Control of gas sample temperature and pressure may be needed to either condition the gas to an appropriate temperature for concentration measurement diagnostic (e.g., laser absorption spectroscopy), or to remove certain compounds (e.g., water vapor) from the sample.

Figure 3A:
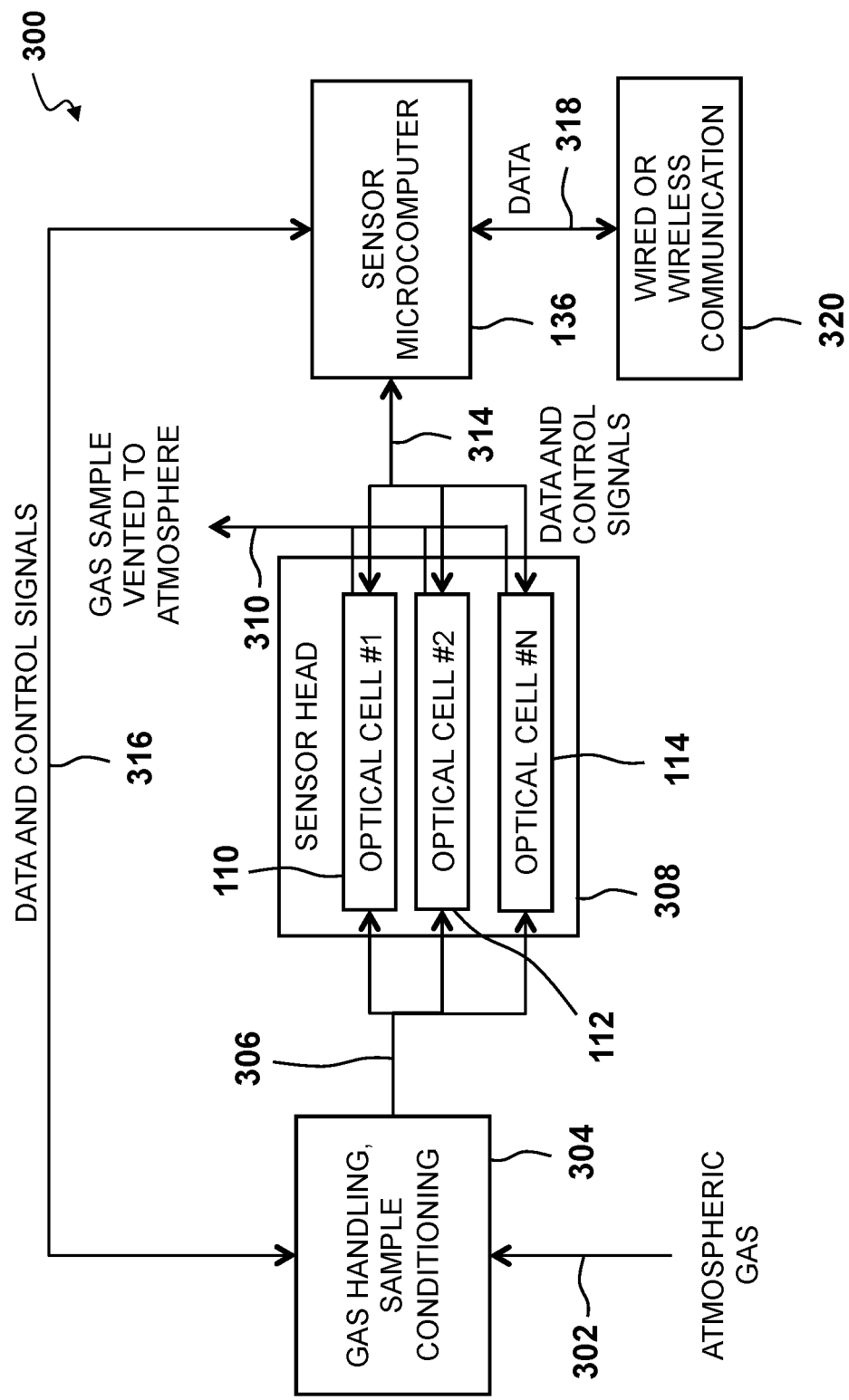
FIG. 3A depicts a block diagram of a gas sensor architecture, according to one embodiment.
Figure 3B:
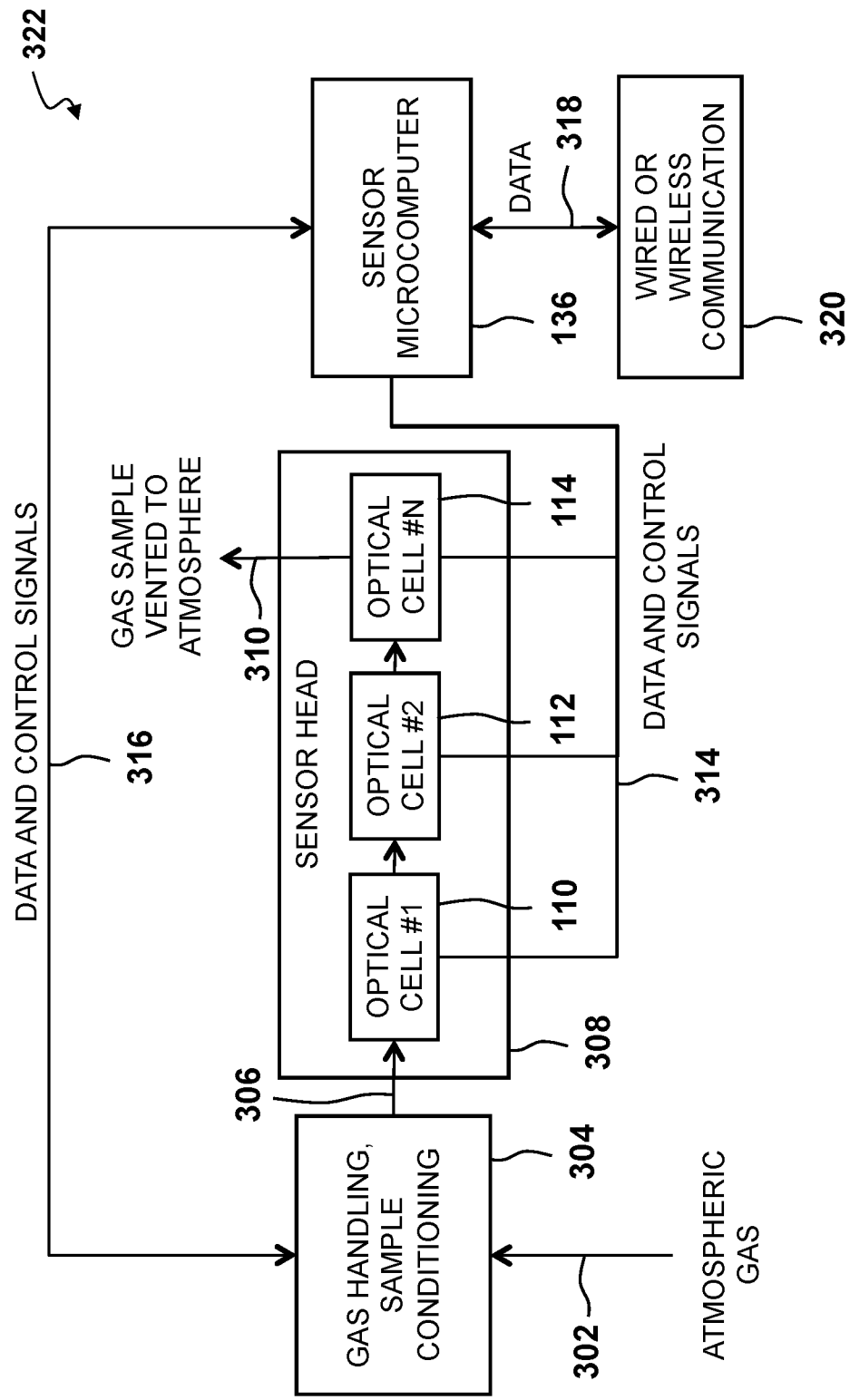
FIG. 3B depicts a block diagram of another gas sensor architecture, according to one embodiment.

The method 200 may then include providing the atmospheric gas to a gas sensor (step 208). In some embodiments, the atmospheric gas may be provided directly to the gas sensor without any gas handling system, temperature modification, and/or pressure modification. The gas sensor may include one or more optical cells. In one embodiment, the optical cells may be connected in series, such as shown in FIG. 3B. In another embodiment, the optical cells may be connected in parallel, such as shown in FIG. 3A. The atmospheric gas provided to the gas sensor may be heated, cooled, increased in pressure, and/or decreased in pressure.

The method 200 may then include detecting, by the one or more optical cells of the gas sensor, gas from one or more of: methane, carbon dioxide, water, hydrogen sulfide, ammonia, sulfur oxides, and nitrogen oxides (step 210). In some embodiments, the gas sensor may only detect one type of gas. In other embodiments, the gas sensor may detect two or more types of gas. In some embodiments, different optical cells may be used to detect different types of gas.

The method 200 may also include recording, by a processor having addressable memory, data from at least one of: an ambient temperature, an ambient pressure, aerial vehicle telemetry, and an aerial vehicle location. This recorded data may correspond to gas detected by the gas sensor (step 212). For example, the processor may record information on the UAV location as well as any detected gas at that location. This data may be later processed to determine gas levels across a range of locations.

The method 200 may then include generating, by the processor, an atmospheric greenhouse gas concentration data on a map based on the detected gas and recorded data (step 214). This map may be a satellite image, aerial image, two-dimensional color map, two-dimensional contour map, and/or three-dimensional topographical surface/mesh map. The recorded data and detected gas may be combined, stored, and further processed.

FIG. 3A depicts a block diagram of a gas sensor architecture 300, according to one embodiment. Atmospheric gas 302 is received by a gas handling, sample conditioning system 304. The gas handling, sample conditioning system 304 may increase the temperature of the atmospheric gas to a set temperature, decrease the temperature of the atmospheric gas to a set temperature, increase the pressure of the atmospheric gas to a set pressure, and/or decrease the pressure of the atmospheric gas to a set pressure. A sensor head 308 of a gas sensor may receive the handled and/or conditioned gas 306. The sensor head 308 may include one or more optical cells 110, 112, 114. Each of the optical cells 110, 112, 114 may be contained in the sensor head 308 with parallel gas flow paths. One the gas flows through the optical cells 110, 112, 114 the gas is vented 310 to atmosphere. Data and control signals 314 from the optical cells 110, 112, 114 are sent to a processor 136, such as a sensor microcomputer. The processor 136 may also send and receive data and control signals 316 with the gas handling, sample conditioning system 304. Data 318 from the processor 136 may be sent via wired and/or wireless communication 320 to another system, such as a cloud server, ground control system (GCS), or the like. The data 318 may contain information on the optical cell 110, 112, 114 readings, temperature and/or pressure of the atmospheric gas 302, temperature and/or pressure of the handled and/or conditioned gas 306, a location of the sensor and/or a location of the UAV the sensor is attached to, and the like.

FIG. 3B depicts a block diagram of another gas sensor architecture 322, according to one embodiment. The optical cells 110, 112, 114 may be housed in the sensor head 308 with a serial gas flow path. In both architectures 300, 322 shown in FIGS. 3A-3B, the processor 136 may interface with the UAV telemetry or other control systems via a wired or wireless connection 320. The processor 136 may also interface with the gas handling and sample conditioning system 304 to send and/or receive data and control signals 316. Atmospheric gas 302 is received by a gas handling, sample conditioning system 304. The gas handling, sample conditioning system 304 may increase the temperature of the atmospheric gas to a set temperature, decrease the temperature of the atmospheric gas to a set temperature, increase the pressure of the atmospheric gas to a set pressure, and/or decrease the pressure of the atmospheric gas to a set pressure. A sensor head 308 of a gas sensor may receive the handled and/or conditioned gas 306. The sensor head 308 may include one or more optical cells 110, 112, 114. Each of the optical cells 110, 112, 114 may be contained in the sensor head 308 with serial gas flow paths. The handled and/or conditioned gas 306 flows to the first optical cell 110, then to the second optical cell 112, then to one or more additional optical cells 114, and then the gas sample is vented 310 to atmosphere. Data and control signals 314 from the optical cells 110, 112, 114 are sent to a processor 136, such as a sensor microcomputer. The processor 136 may also send and receive data and control signals 316 with the gas handling, sample conditioning system 304. Data 318 from the processor 136 may be sent via wired and/or wireless communication 320 to another system, such as a cloud server, GCS, or the like. The data 318 may contain information on the optical cell 110, 112, 114 readings, temperature and/or pressure of the atmospheric gas 302, temperature and/or pressure of the handled and/or conditioned gas 306, a location of the sensor and/or a location of the UAV the sensor is attached to, and the like.

Figure 4:
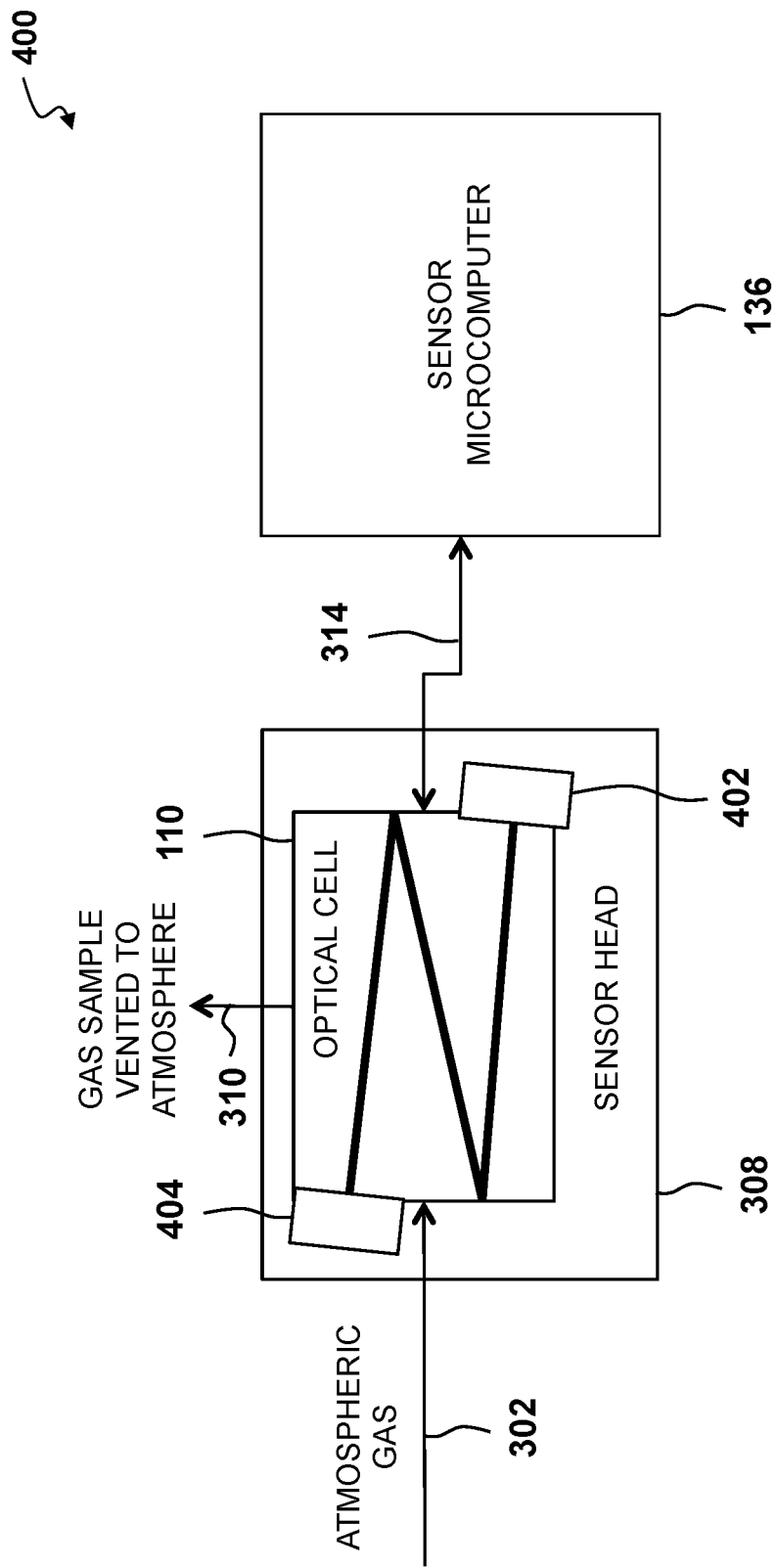
FIG. 4 depicts a single optical cell configuration, according to one embodiment.

FIG. 4 depicts a single optical cell configuration 400, according to one embodiment. Atmospheric gas 302 enters the optical cell 110 in the sensor head 308 and is then vented 310 to the atmosphere. A detector 402 is capable of sensing light from a laser 404. The path the light travels from the laser 404 to the detector 402 is dictated by the optical elements used in the optical cell 110. In some embodiments, the optical elements may be the end caps of the cell. In other embodiments, the optical elements may make up the body of the optical cell. Data and control signals 314 from the optical cell 110, sensor head 308, and/or detector 402 may be sent to a sensor microcomputer 136 for processing.

FIG. 5A depicts a gas sensor 102 mounted on an aerial vehicle 104 and receiving gas samples from relatively high-pressure zones and venting the gas samples to relatively low pressure zones, according to one embodiment.

Sampling of atmospheric air can be achieved through naturally occurring pressure differences around the airframe, by piping gas samples from relatively high pressure zones to relatively low pressure zones. A high pressure zone may be on a top surface of the aerial vehicle 104. A medium pressure zone may be on a bottom surface of the aerial vehicle 104. A low pressure zone may be proximate a wing tip of the aerial vehicle 104.

FIG. 5B depicts a gas sensor 102 mounted on a quadcopter UAV 104 and receiving gas samples from a gas handling system 116, according to one embodiment. If relative pressure differentials are inconsistent during all stages of flight, such as on a quadcopter 104, then a gas handling system 116 using a pump on-board the flight platform may be used to draw in and pump the atmospheric sample.

FIG. 5C depicts a gas sensor mounted on an aerial vehicle 104 and receiving gas samples from a gas handling system 116 where relative pressure differentials may be inconsistent given a prescribed flight envelope, according to one embodiment. The sensor 102 and payload may be located on different parts of an aerial vehicle, such as a UAV or quadcopter. Depending on the use, the sensor 102 may receive gas samples during normal flight or require an additional pump from the gas handling system 116.

Figure 6B:
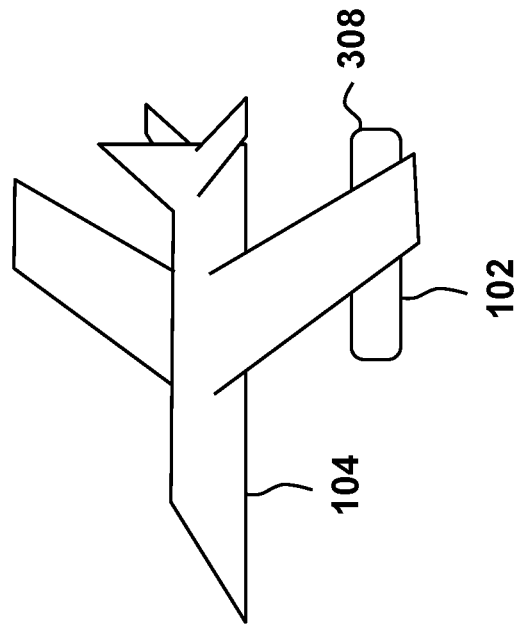
FIG. 6B depicts a gas sensor mounted on an aerial vehicle externally on a wing or pylon of the aerial vehicle, according to one embodiment.
Figure 6A:
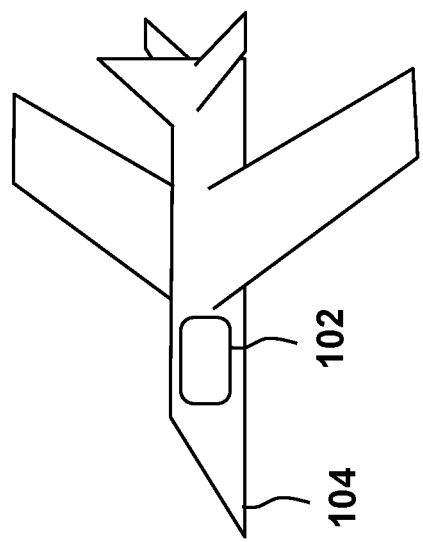
FIG. 6A depicts a gas sensor mounted on an aerial vehicle within the payload bay of the aerial vehicle, according to one embodiment.

FIG. 6A depicts a gas sensor 102 mounted on an aerial vehicle 104 within the payload bay of the aerial vehicle, according to one embodiment. The gas sensor 102 may be mounted in, or proximate to, the fuselage of the aerial vehicle 104 in some embodiments.

FIG. 6B depicts a gas sensor 102 mounted on an aerial vehicle 104 externally on a wing or pylon of the aerial vehicle, according to one embodiment. The gas sensor 102 and any supporting hardware may be mounted within a payload bay of the UAV, externally on a wing or pylon, or any other portion of a UAV to provide gas samples. The sensor head 308 may be mounted distal from a fuselage of the aerial vehicle 104 so as to minimize turbulence, increase gas sensor accuracy 102, or the like.

Figure 7:
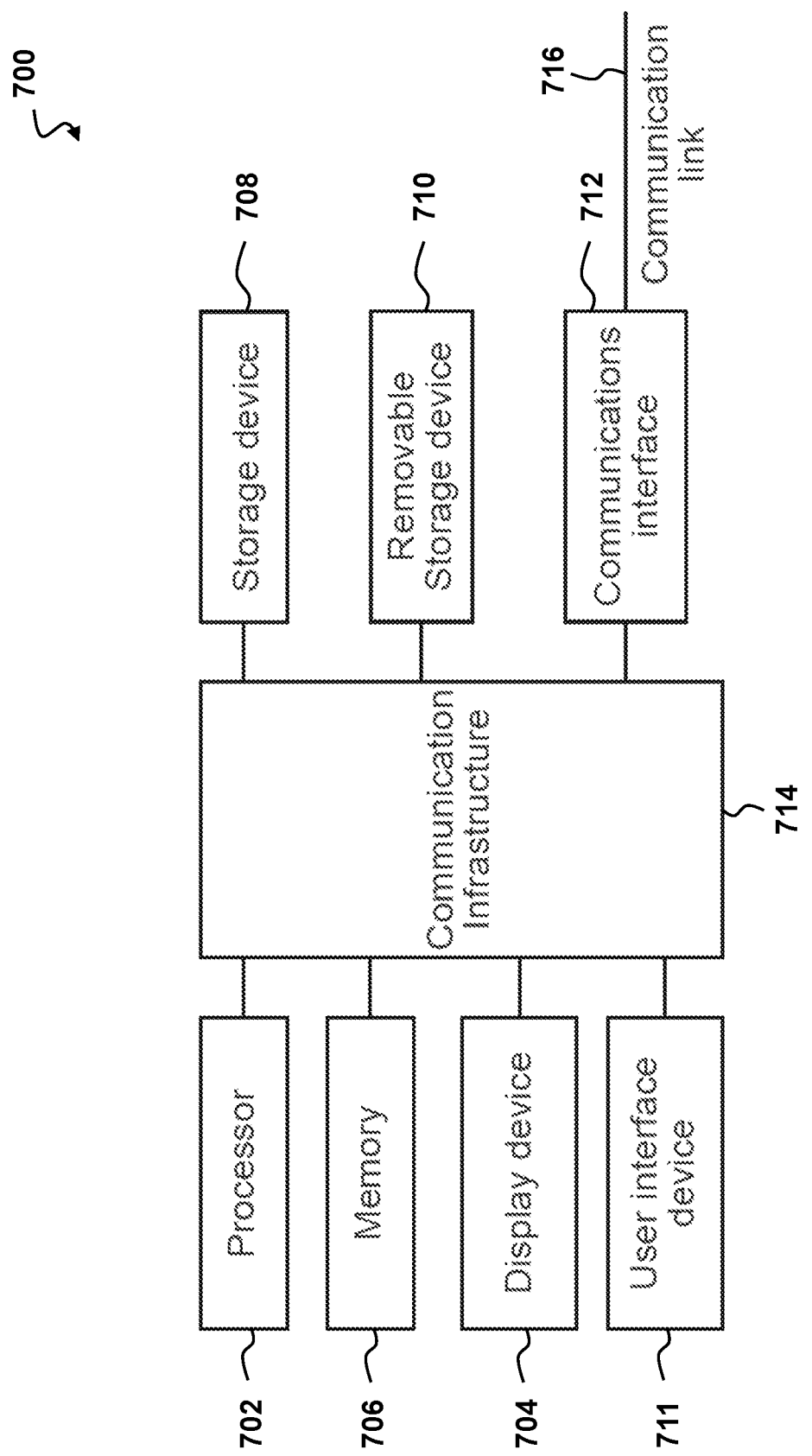
FIG. 7 shows a high-level block diagram and process of a computing system for implementing an embodiment of the system and process.

FIG. 7 is a high-level block diagram 700 showing a computing system comprising a computer system useful for implementing an embodiment of the system and process, disclosed herein. Embodiments of the system may be implemented in different computing environments. The computer system includes one or more processors 702, and can further include an electronic display device 704 (e.g., for displaying graphics, text, and other data), a main memory 706 (e.g., random access memory (RAM)), storage device 708, a removable storage device 710 (e.g., removable storage drive, a removable memory module, a magnetic tape drive, an optical disk drive, a computer readable medium having stored therein computer software and/or data), user interface device 711 (e.g., keyboard, touch screen, keypad, pointing device), and a communication interface 712 (e.g., modem, a network interface (such as an Ethernet card), a communications port, or a PCMCIA slot and card). The communication interface 712 allows software and data to be transferred between the computer system and external devices. The system further includes a communications infrastructure 714 (e.g., a communications bus, cross-over bar, or network) to which the aforementioned devices and modules are connected as shown.

Information transferred via communications interface 714 may be in the form of signals such as electronic, electromagnetic, optical, or other signals capable of being received by communications interface 714, via a communication link 716 that carries signals and may be implemented using wire or cable, fiber optics, a phone line, a cellular/mobile phone link, a radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

The computer system 700 described above services, but is not limited to, several purposes. The computer system 700 may control the gas sensor. The computer system 700 may interface with UAV telemetry. The computer system 700 may interface with a ground control station (GCS). In certain embodiments, the computer system 700 may adjust the gas sensor operating parameters, e.g., the sensor sampling rate, based on information collected from UAV telemetry or the ground control station. For example, the computer may increase a gas sensor sampling rate to adjust for increased UAV speed so as to maintain a constant spatial distribution of sampled locations. As another example, the computer may increase sampling rate if the computer infers that the UAV is traversing part of the atmosphere with relatively high turbulence.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 712. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 8:
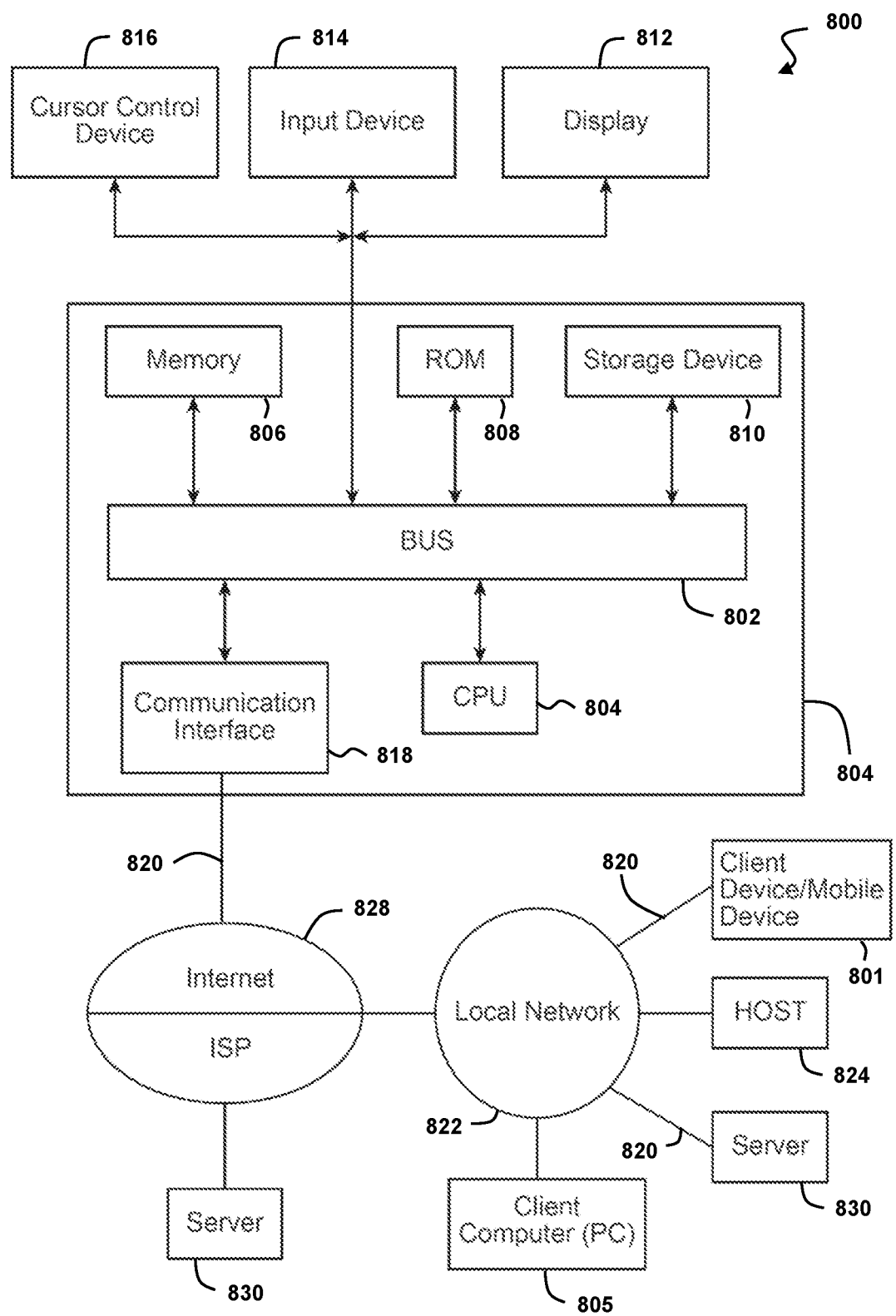
FIG. 8 shows a block diagram and process of an exemplary system in which an embodiment may be implemented.

FIG. 8 shows a block diagram of an example system 800 in which an embodiment may be implemented. The system 800 includes one or more client devices 801 such as consumer electronics devices, connected to one or more server computing systems 830. A server 830 includes a bus 802 or other communication mechanism for communicating information, and a processor (CPU) 804 coupled with the bus 802 for processing information. The server 830 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution or instructions to be executed by the processor 804. The server computer system 830 further includes a read only memory (ROM) 808 or other static storage device coupled to the bus 802 for storing static information and instructions for the processor 804. A storage device 810, such as a magnetic disk or optical disk, is provided and coupled to the bus 802 for storing information and instructions. The bus 802 may contain, for example, thirty-two address lines for addressing video memory or main memory 806. The bus 802 can also include, for example, a 32-bit data bus for transferring data between and among the components, such as the CPU 804, the main memory 806, video memory and the storage 810. Alternatively, multiplex data/address lines may be used instead of separate data and address lines.

The server 830 may be coupled via the bus 802 to a display 812 for displaying information to a computer user. An input device 814, including alphanumeric and other keys, is coupled to the bus 802 for communicating information and command selections to the processor 804. Another type or user input device comprises cursor control 816, such as a mouse, a trackball, or cursor direction keys for communicating direction information and command selections to the processor 804 and for controlling cursor movement on the display 812.

According to one embodiment, the functions are performed by the processor 804 executing one or more sequences of one or more instructions contained in the main memory 806. Such instructions may be read into the main memory 806 from another computer-readable medium, such as the storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the server 830 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received from the main memory 806 may optionally be stored on the storage device 810 either before or after execution by the processor 804.

The server 830 also includes a communication interface 818 coupled to the bus 802. The communication interface 818 provides a two-way data communication coupling to a network link 820 that is connected to the world wide packet data communication network now commonly referred to as the Internet 828. The Internet 828 uses electrical, electromagnetic or optical signals that carry digital data streams. The signals through the various networks and the signals on the network link 820 and through the communication interface 818, which carry the digital data to and from the server 830, are exemplary forms or carrier waves transporting the information.

In another embodiment of the server 830, interface 818 is connected to a network 822 via a communication link 820. For example, the communication interface 818 may be an integrated services digital network (ISDN) card or a modem to provide a data communication connection to a corresponding type of telephone line, which can comprise part of the network link 820. As another example, the communication interface 818 may be a local area network (LAN) card to provide a data communication connection to a compatible LAN. Wireless links may also be implemented. In any such implementation, the communication interface 818 sends and receives electrical electromagnetic or optical signals that carry digital data streams representing various types of information.

The network link 820 typically provides data communication through one or more networks to other data devices. For example, the network link 820 may provide a connection through the local network 822 to a host computer 824 or to data equipment operated by an Internet Service Provider (ISP). The ISP in turn provides data communication services through the Internet 828. The local network 822 and the Internet 828 both use electrical, electromagnetic or optical signals that carry digital data streams. The signals through the various networks and the signals on the network link 820 and through the communication interface 818, which carry the digital data to and from the server 830, are exemplary forms or carrier waves transporting the information.

The server 830 can send/receive messages and data, including e-mail, program code, through the network, the network link 820 and the communication interface 818. Further, the communication interface 818 can comprise a USB/Tuner and the network link 820 may be an antenna or cable for connecting the server 830 to a cable provider, satellite provider or other terrestrial transmission system for receiving messages, data and program code from another source.

The example versions of the embodiments described herein may be implemented as logical operations in a distributed processing system such as the system 800 including the servers 830. The logical operations of the embodiments may be implemented as a sequence of steps executing in the server 830, and as interconnected machine modules within the system 800. The implementation is a matter of choice and can depend on performance of the system 800 implementing the embodiments. As such, the logical operations constituting said example versions of the embodiments are referred to for e.g., as operations, steps or modules.

Similar to a server 830 described above, a client device 801 can include a processor, memory, storage device, display, input device and communication interface (e.g., e-mail interface) for connecting the client device to the Internet 828, the ISP, or LAN 822, for communication with the servers 830.

The system 800 can further include computers (e.g., personal computers, computing nodes) 805 operating in the same manner as client devices 801, wherein a user can utilize one or more computers 805 to manage data in the server 830.

Figure 9:
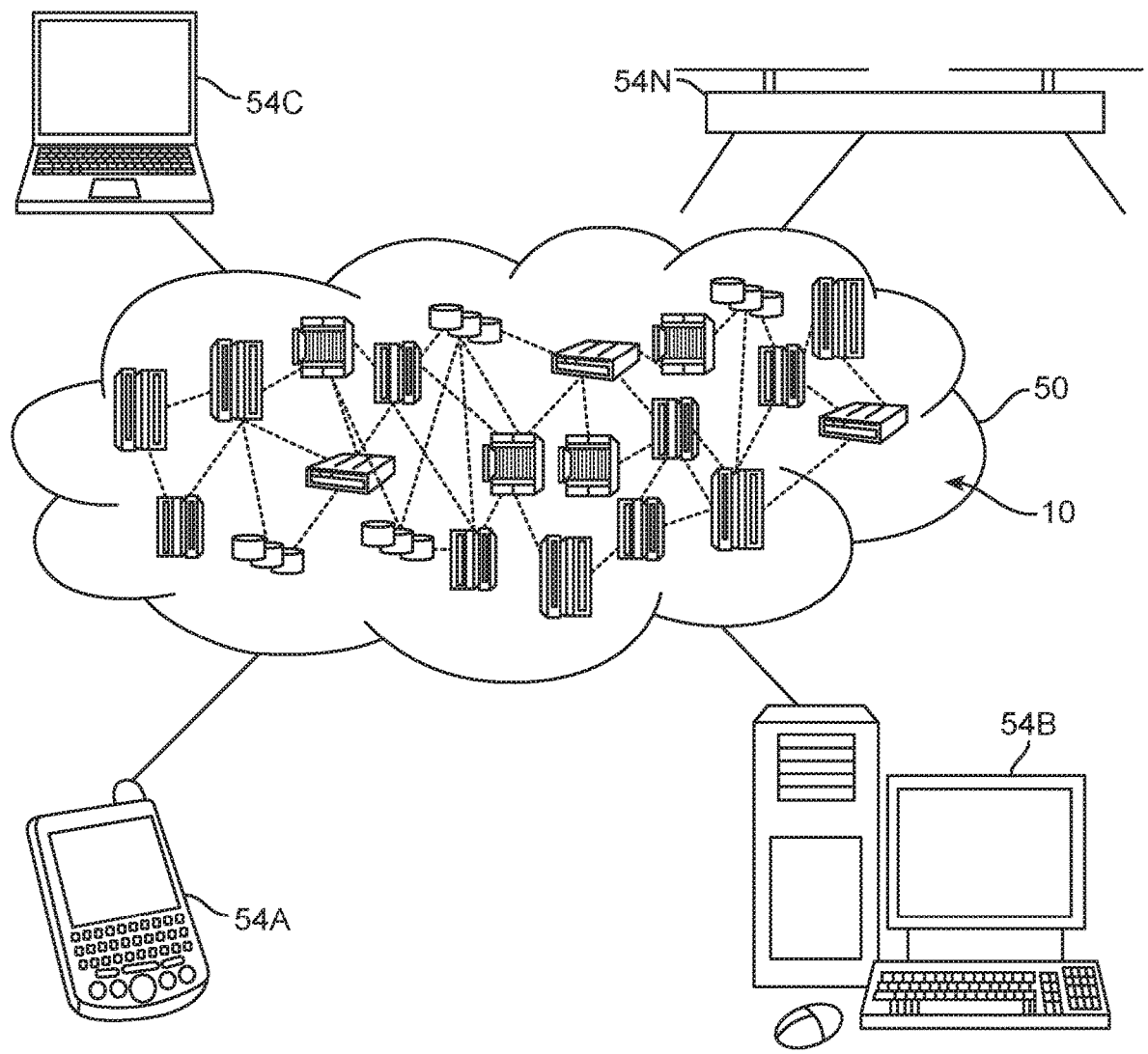
FIG. 9 depicts a cloud computing environment for implementing an embodiment of the system and process disclosed herein

Referring now to FIG. 9, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smart watch, set-top box, video game system, tablet, mobile computing device, or cellular telephone 54A, desktop computer 54B, laptop computer 54C, and/or unmanned aerial vehicle (UAV) 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 10 are intended to be illustrative only and that computing nodes 10 and cloud computing environment 50 can communicate with any type of computerized device over any type of network and/or network addressable connection (e.g., using a web browser).

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention herein disclosed by way of examples should not be limited by the particular disclosed embodiments described above.

What is claimed is:

1. A system comprising:
    a trace-gas sensor configured for transport by an aerial vehicle, wherein the trace-gas sensor is configured to receive gas samples at different locations, and wherein the trace-gas sensor comprises:
    a thermal chamber;
    a pressure regulator;
    a sensor head;
    a gas conditioning system configured to receive the gas samples and control the gas samples to a specific temperature by the thermal chamber and to a set pressure by the pressure regulator, before the gas sample reaches the sensor head of the trace-gas sensor; and
    a plurality of optical cells housed in the sensor head that are configured to receive a conditioned gas samples from the gas conditioning system, wherein the optical cells are configured to detect trace-gas in the conditioned gas sample under the controlled temperature and the controlled pressure inside the sensor head, wherein at least one first optical cell of the optical cells is tuned to detect hydrocarbon gas species in the conditioned gas sample, wherein at least one second optical cell of the optical cells is tuned to detect non-hydrocarbon gas species in the conditioned gas sample, wherein the at least one first optical cell and the at least one second optical cell are connected either in parallel or series, and wherein the at least one first optical cell and the at least one second optical cell are at least one of: connected in parallel through parallel gas flow paths so that the conditioned gas sample from the gas conditioning system is divided to flow to each of the at least one first optical cell and the at least one second optical cell, respectively, and connected in series through serial gas flow paths so that the conditioned gas sample from the gas conditioning system flows to a front located optical cell of the at least one first optical cell and the at least one second optical cell and then the conditioned gas sample from the front located optical cell flows to a next located optical cell of the at least one first optical cell and the at least one second optical cell; and
    a processor having addressable memory, the processor configured to:
    detect the trace-gas from the optical cells of the trace-gas sensor;
    record data corresponding to the detected trace-gas, wherein the recorded data comprises at least one of: an ambient temperature from a temperature sensor, an ambient pressure from a pressure sensor, an aerial vehicle telemetry, and an aerial vehicle location of the aerial vehicle from a global positioning system (GPS);
    generate a map of trace-gas concentration on a display based on the detected trace-gas and the recorded data, wherein the map of trace-gas concentration is generated on at least one of: a satellite image, an aerial image, a two-dimensional color map, a two-dimensional contour map, a three-dimensional topographical surface map, and a three-dimensional topographical mesh map; and
    display the generated map of trace-gas concentration on the display.

2. The system of claim 1 further comprising:
    a trace-gas handling system configured to supply trace-gas to the trace-gas sensor, wherein the detected trace-gas is one or more of: methane, carbon dioxide, hydrogen sulfide, water, ammonia, sulfur oxides, and nitrogen, wherein the trace gas sensor comprises an ultra-lightweight, low power, part-per-billion (ppb) sensitivity, mid-Infrared (wavelength $\lambda$=3-8 µm), open path gas concentration sensor.

3. The system of claim 2, wherein the trace-gas handling system comprises at least one of: a pump, a ram-air design, and a velocity-induced vacuum.

4. The system of claim 2 further comprising:
a thermal chamber configured to modify a temperature of the supplied trace-gas to a set temperature, wherein the temperature sensor is configured to measure the temperature of the supplied trace-gas.

5. The system of claim 2 further comprising:
a pressure regulator configured to modify a pressure of the supplied trace-gas to a set pressure, wherein the pressure sensor is configured to measure the pressure of the supplied trace-gas.

6. The system of claim 1, wherein the processor is further configured to:
actively adjust at least one operating parameter of the trace-gas sensor based on the recorded data.

7. The system of claim 6, wherein the at least one operating parameter of the trace-gas sensor is an acquisition rate.

8. The system of claim 7, wherein the acquisition rate is increased by the processor based on an increased speed of an aerial vehicle from the recorded data of the aerial vehicle location to maintain a substantially constant spatial distribution of sampled locations.

9. The system of claim 7, wherein the acquisition rate is increased by the processor based on an aerial vehicle traversing an area with increased turbulence based on the recorded data.

10. The system of claim 1, wherein the trace-gas sensor is mounted on the aerial vehicle.

11. The system of claim 1, wherein the aerial vehicle is an unmanned aerial vehicle (UAV).

12. The system of claim 1, wherein the trace-gas sensor is mounted in a fuselage of the aerial vehicle.

13. The system of claim 1, wherein the trace-gas sensor is mounted distal from a fuselage of the aerial vehicle.

14. The system of claim 1, further comprising:
a ground control station (GCS) in communication with the trace-gas sensor, the GCS comprising a GCS processor having addressable memory, the GCS processor configured to:
receive the detected trace-gas from the one or more optical cells of the trace-gas sensor;
receive the recorded data corresponding to the detected trace-gas; and
provide instructions to the aerial vehicle to follow a flight path.

15. The system of claim 1, further comprising:
a power management and laser control logic system configured to supply a laser of each of the one or more optical cells with a drive current, an operating temperature, and a power consumption within operating bounds of each laser.

16. A method comprising:
providing a gas sample comprising a trace-gas to a trace-gas sensor configured for transport by an aerial vehicle, wherein a sensor head houses optical cells of the trace-gas sensor;
controlling the gas sample to have a set temperature by a thermal chamber, before the gas sample reaches the sensor head of the trace-gas sensor;
controlling the gas sample to have a controlled pressure by a pressure regulator, before the gas sample reaches the sensor head of the trace-gas sensor;
detecting, by the optical cells of the trace-gas sensor, trace-gas in a conditioned gas sample under the controlled temperature and the controlled pressure inside the sensor head, wherein at least one first optical cell of the optical cells is tuned to detect hydrocarbon gas species in the gas sample, wherein at least one second optical cell of the optical cells is tuned to detect non-hydrocarbon gas species in the gas sample, and wherein the at least one first optical cell and at least one second optical cell are connected either in parallel or series, and wherein the at least one first optical cell and the at least one second optical cell are at least one of: connected in parallel through parallel gas flow paths so that the conditioned gas sample from the gas conditioning system is divided to flow to each of the at least one first optical cell and the at least one second optical cell, respectively, and connected in series through serial gas flow paths so that the conditioned gas sample from the gas conditioning system flows to a front located optical cell of the at least one first optical cell and the at least one second optical cell and then the conditioned gas sample from the front located optical cell flows to a next located optical cell of the at least one first optical cell and the at least one second optical cell;
recording, by a processor having addressable memory, data corresponding to the detected trace-gas from at least one of: an ambient temperature, an ambient pressure, an aerial vehicle telemetry, and an aerial vehicle location;
generating, by the processor, a map of trace-gas concentration data on a display based on the detected trace-gas and recorded data, wherein the map of trace-gas concentration is generated on at least one of: a satellite image, an aerial image, a two-dimensional color map, a two-dimensional contour map, a three-dimensional topographical surface map, and a three-dimensional topographical mesh map; and
displaying, by the processor on the display, the generated map of trace-gas concentration data.

17. The method of claim 16 further comprising, prior to providing the trace-gas to the trace-gas sensor:
receiving trace-gas from a trace-gas handling system, wherein the trace-gas is one or more of: methane, carbon dioxide, water, hydrogen sulfide, ammonia, sulfur oxides, and nitrogen oxides.

18. The method of claim 17 further comprising, prior to providing the trace-gas to the trace-gas sensor:
measuring or inferring a temperature of the received trace-gas from the trace-gas handling system; and
modifying the temperature of the received trace-gas to a set temperature via a thermal chamber.

19. The method of claim 17 further comprising, prior to providing the trace-gas to the trace-gas sensor:
measuring or inferring a pressure of the received trace-gas from the trace-gas handling system; and
modifying the pressure of the received trace-gas to a set pressure via a pressure regulator.

20. A system comprising:
an unmanned aerial vehicle (UAV);
a trace-gas handling system configured to receive gas samples each including trace gas at different locations and supply the gas samples each including trace-gas to a trace-gas sensor;

a thermal chamber configured to modify a temperature of the supplied trace-gas to a set temperature before the gas sample reaches a sensor head of the trace-gas sensor;

a pressure regulator configured to modify a pressure of the supplied trace-gas to a set pressure before the gas sample reaches the sensor head of the trace-gas sensor;

a sensor head;

a plurality of optical cells of the trace-gas sensor housed in the sensor head, wherein the optical cells are configured to receive a conditioned gas sample from the thermal chamber and the pressure regulator, wherein the optical cells are configured to detect trace-gas in the conditioned gas sample under the controlled temperature and the controlled pressure inside the sensor head, wherein the trace-gas sensor is configured for transport by the UAV, wherein at least one first optical cell of the optical cells is tuned to detect hydrocarbon gas species in the gas sample, wherein at least one second optical cell of the optical cells is tuned to detect non-hydrocarbon gas species in the gas sample, and wherein the at least one first optical cell and at least one second optical cell are connected either in parallel or series, and wherein the at least one first optical cell and the at least one second optical cell are at least one of: connected in parallel through parallel gas flow paths so that the conditioned gas sample from the gas conditioning system is divided to flow to each of the at least one first optical cell and the at least one second optical cell, respectively, and connected in series through serial gas flow paths so that the conditioned gas sample from the gas conditioning system flows to a front located optical cell of the at least one first optical cell and the at least one second optical cell and then the conditioned gas sample from the front located optical cell flows to a next located optical cell of the at least one first optical cell and the at least one second optical cell; and a processor having addressable memory, the processor configured to:

detect trace-gas from the optical cells of the trace-gas sensor, wherein the detected trace-gas is one or more of: methane, carbon dioxide, hydrogen sulfide, water, ammonia, sulfur oxides, and nitrogen;

record data corresponding to the detected trace-gas, wherein the recorded data comprises at least one of: an ambient temperature from a temperature sensor, an ambient pressure from a pressure sensor, an aerial vehicle telemetry, and an aerial vehicle location from a global positioning system (GPS);

actively adjust at least one operating parameter of the trace-gas sensor based on the recorded data;

generate a map of trace-gas concentration based on the detected trace-gas and the recorded data, wherein the map of trace-gas concentration is generated on at least one of: a satellite image, an aerial image, a two-dimensional color map, a two-dimensional contour map, a three-dimensional topographical surface map, and a three-dimensional topographical mesh map; and display the generated map of trace-gas concentration on the display.

* * * * *